US012181401B2

(12) United States Patent
Kottapalli et al.

(10) Patent No.: US 12,181,401 B2
(45) Date of Patent: Dec. 31, 2024

(54) TRACER DETECTION SYSTEM AND METHOD FOR CHARACTERIZING EFFECTIVENESS OF AIR REMOVAL IN AN AEROSOL ZONE

(71) Applicant: Poppy Health, Inc., Mountain View, CA (US)

(72) Inventors: Kalyan Kottapalli, Mountain View, CA (US); Sam Molyneux, Mountain View, CA (US); Konrad Swic, Mountain View, CA (US); Elizabeth Caley, Mountain View, CA (US); Aaron Botham, Mountain View, CA (US)

(73) Assignee: Poppy Health, Inc., Mountain View, CA (US)

( * ) Notice: Subject to any disclaimer, the term of this patent is extended or adjusted under 35 U.S.C. 154(b) by 0 days.

(21) Appl. No.: 18/244,775

(22) Filed: Sep. 11, 2023

(65) Prior Publication Data

US 2023/0417646 A1 Dec. 28, 2023

Related U.S. Application Data

(63) Continuation-in-part of application No. PCT/US2023/032351, filed on Sep. 8, 2023, which is
(Continued)

(51) Int. Cl.
*G01N 15/06* (2024.01)
*F24F 11/30* (2018.01)
(Continued)

(52) U.S. Cl.
CPC ............. *G01N 15/06* (2013.01); *F24F 11/30* (2018.01); *G01N 33/0027* (2013.01); *F24F 2110/64* (2018.01)

(58) Field of Classification Search
None
See application file for complete search history.

(56) References Cited

U.S. PATENT DOCUMENTS 917,178 A 4/1909 Spitz et al.
4,367,950 A 1/1983 Klug
(Continued)

FOREIGN PATENT DOCUMENTS

CN 111662816 A 9/2020
CN 112014528 A 12/2020
(Continued)

OTHER PUBLICATIONS

International Search Report and Written Opinion for International Application No. PCT/US23/32351 mailed on Jan. 31, 2024; 21 pages.
(Continued)

*Primary Examiner* — Peter J Macchiarolo
*Assistant Examiner* — Gedeon M Kidanu
(74) *Attorney, Agent, or Firm* — Run8 Patent Group, LLC; Peter Miller

(57) ABSTRACT

One variation of a method includes, during execution of a tracer test: triggering release of a tracer load into air in an aerosol zone by a dispenser transiently arranged in the aerosol zone, the tracer load including a concentration of aerosol tracers; and recording a timeseries of aerosol data via a sensor unit transiently arranged in the aerosol zone, the timeseries of aerosol data representing concentrations of aerosol particles present in air. The method further includes: based on the timeseries of aerosol data and the concentration, deriving a tracer concentration curve representing change in concentration of aerosol tracer particles; based on characteristics of the tracer concentration curve, deriving an airflow value representing removal of aerosol particles from
(Continued)

the aerosol zone during the tracer test; and interpreting an outcome for the tracer test based on a difference between the airflow value and a target airflow value defined for the aerosol zone.

17 Claims, 8 Drawing Sheets

Related U.S. Application Data a continuation-in-part of application No. 18/077,185, filed on Dec. 7, 2022, application No. 18/244,775 is a continuation-in-part of application No. 18/077,185, filed on Dec. 7, 2022.

(60) Provisional application No. 63/405,340, filed on Sep. 9, 2022, provisional application No. 63/355,949, filed on Jun. 27, 2022, provisional application No. 63/329,717, filed on Apr. 11, 2022, provisional application No. 63/286,821, filed on Dec. 7, 2021, provisional application No. 63/286,815, filed on Dec. 7, 2021, provisional application No. 63/286,806, filed on Dec. 7, 2021.

(51) Int. Cl.
*F24F 110/64* (2018.01)
*G01N 33/00* (2006.01)

(56) References Cited

U.S. PATENT DOCUMENTS

| | | | |
|---|---|---|---|
| 5,150,036 | A | 9/1992 | Pourprix |
| 5,421,214 | A | 6/1995 | Burgdorfer |
| 6,363,769 | B2 | 4/2002 | Krajewski et al. |
| 6,686,999 | B2 | 2/2004 | Ketkar |
| 6,974,669 | B2 | 12/2005 | Mirkin et al. |
| 7,029,921 | B2 | 4/2006 | Lee et al. |
| 7,389,158 | B2 | 6/2008 | Desrochers et al. |
| 7,578,973 | B2 | 8/2009 | Call et al. |
| 7,633,606 | B2 | 12/2009 | Northrup et al. |
| 7,973,929 | B2 | 7/2011 | Bates |
| 8,173,431 | B1 | 5/2012 | Call |
| 8,272,280 | B2 | 9/2012 | Jones, Jr. |
| 8,539,840 | B2 | 9/2013 | Ariessohn et al. |
| 8,578,796 | B2 | 11/2013 | Cho |
| 8,642,954 | B2 | 2/2014 | Ivaldi et al. |
| 8,687,191 | B2 | 4/2014 | Altobelli et al. |
| 8,689,648 | B1 | 4/2014 | Heff |
| 9,063,040 | B2 | 6/2015 | Calio et al. |
| 9,170,178 | B2 | 10/2015 | Sobek |
| 9,261,885 | B2 | 2/2016 | Tryfonos et al. |
| 9,689,792 | B1 | 6/2017 | Sickenberger et al. |
| 9,989,445 | B2 | 6/2018 | Ligugnana et al. |
| 10,919,047 | B2 | 2/2021 | Mainelis et al. |
| 10,928,389 | B2 | 2/2021 | Fan et al. |
| 11,300,484 | B1 | 4/2022 | Bango |
| 11,365,409 | B2 | 6/2022 | Shum et al. |
| 11,366,116 | B1 | 6/2022 | Meagher et al. |
| 2002/0012611 | A1 | 1/2002 | Stylli et al. |
| 2005/0032241 | A1 | 2/2005 | Coassin et al. |
| 2005/0042604 | A1 | 2/2005 | Tong et al. |
| 2005/0255600 | A1 | 11/2005 | Padmanabhan et al. |
| 2006/0040286 | A1 | 2/2006 | Mirkin et al. |
| 2006/0060006 | A1 | 3/2006 | Ornath et al. |
| 2008/0014576 | A1 | 1/2008 | Jovanovich et al. |
| 2008/0281528 | A1 | 11/2008 | Relle, Jr. |
| 2011/0251084 | A1 * | 10/2011 | Brenan ................ G01N 33/569 435/6.15 |
| 2011/0252897 | A1 | 10/2011 | Swenson et al. |
| 2012/0174650 | A1 | 7/2012 | Ariessohn et al. |
| 2013/0045496 | A1 | 2/2013 | Jansen |
| 2013/0234053 | A1 | 9/2013 | Thomas et al. |
| 2016/0362730 | A1 | 12/2016 | Alexander et al. |
| 2017/0284934 | A1 | 10/2017 | Wang et al. |
| 2018/0155771 | A1 | 6/2018 | Takahashi et al. |
| 2018/0305772 | A1 | 10/2018 | Gilbert et al. |
| 2019/0025299 | A1 | 1/2019 | Vigneault et al. |
| 2019/0257737 | A1 | 8/2019 | Clayton et al. |
| 2020/0179932 | A1 | 6/2020 | Williams et al. |
| 2021/0208062 | A1 | 7/2021 | Linden |
| 2021/0324485 | A1 | 10/2021 | Hodges et al. |
| 2022/0034763 | A1 | 2/2022 | Dutta |
| 2022/0091010 | A1 | 3/2022 | Wystup et al. |
| 2023/0176024 | A1 | 6/2023 | Molyneux et al. |

FOREIGN PATENT DOCUMENTS

| | | | |
|---|---|---|---|
| DE | 102012101063 | A1 | 8/2013 |
| JP | 2017096727 | A | 6/2017 |
| KR | 20110097199 | A | 8/2011 |
| WO | 2006060872 | A1 | 6/2006 |
| WO | 2005029003 | A3 | 5/2007 |
| WO | 2019018559 | A1 | 1/2019 |
| WO | 2019046347 | A9 | 7/2019 |
| WO | 2022047340 | A1 | 3/2022 |
| WO | 2022081543 | A1 | 4/2022 |

OTHER PUBLICATIONS

International Search Report and Written Opinion for International Patent Application PCT/US2022/026201 mailed on Oct. 5, 2022; 14 pages.
Izadyar et al. Ventilation strategies and design impacts on indoor airborne transmission: A review. May 6, 2022 (May 6, 2022). [retrieved on Nov. 17, 2023]. Retrieved from the Internet: pp. 1-19.
M. Z. Bazant, J. W. Bush, A guideline to limit indoor airborne transmission of covid-19. Proceedings of the National Academy of Sciences. 118 (2021), doi:10.1073/pnas.2018995118.
Non-Final Office Action for U.S. Appl. No. 17/728,809 dated Dec. 21, 2022.
Notice of Allowance and Fees Due for U.S. Appl. No. 17/728,823 dated Sep. 2, 2022.
Notice of Allowance and Fees Due for U.S. Appl. No. 18/071,392 dated Apr. 3, 2023.
W. John Kress et al. "DNA barcodes, Genes, genomics, and bioinformatics", The Proceedings of the National Academy of Sciences, vol. 105, 8, Feb. 26, 2008.
Notification of the International Application Number and of the International Filing Date for International Patent Application PCT/US23/32351 mailed on Oct. 2, 2023; 1 page.

* cited by examiner

TARGET VOLUMETRIC AIRFLOW: $VA_T$ [FOR ALL SENSOR UNITS]

$$VA_T = E_{CAi} \times P_Z$$

TARGET AIR CHANGE RATE: ($ACH_T$)

$$ACH_T = \frac{60 \times VA_T}{V_Z}$$

$VA_T$ = TARGET VOLUMETRIC AIRFLOW (PER SENSOR UNIT)
$ECA_i$ = TARGET EQUIVALENT CLEAN AIRFLOW RATE (PER PERSON)
$P_Z$ = OCCUPANCY OF AEROSOL ZONE
$V$ = VOLUME OF AEROSOL ZONE
$ACH_T$ = TARGET AIR-CHANGE RATE (PER SENSOR UNIT)

AREA UNDER THE TARGET DECAY CURVE ($AUC_T$)

BASELINE TARGET, $AUC_{B(T)}$: CALCULATE AREA UNDER THE CURVE USING THE AVERAGE BACKGROUND VALUE EXTRAPOLATED OVER TARGET DECAY PERIOD [$t_I$ TO $t_{F(T)}$]

CONSTANT a:

$$a = \frac{C_I}{e^{-ACH_T \times t}}$$

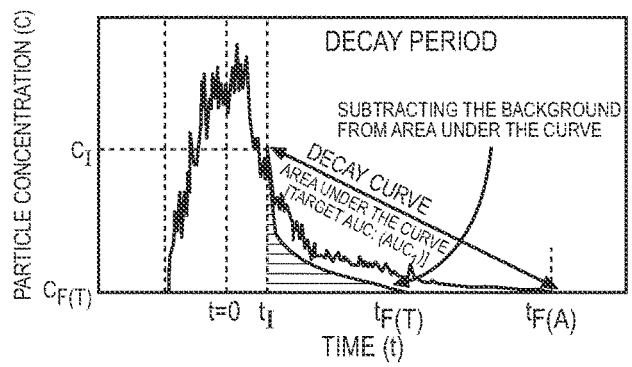

PARTICLE CONCENTRATION (C)

$$C = ae^{-ACH_T \times t}$$

$AUC_T$ $$AUC_T = \sum_{n=0}^{n=t_{F(T)}} \frac{(t_{n+1} - t_n)(C_{n+1} - C_n)}{2} - AUC_{B(T)}$$

$t_I$ = TIME AT START OF DECAY PERIOD
$C_I$ = PARTICLE CONCENTRATION AT $t_I$
$t_{F(T)}$ = TIME AT END OF TARGET DECAY PERIOD
$C_{F(T)}$ = PARTICLE CONCENTRATION AT $t_{F(T)}$
n = TIME STEPS
$AUC_{B(T)}$ = AREA UNDER THE BASELINE TARGET CURVE

*FIGURE 3A*

VOLUMETRIC AIRFLOW, $V_A$

[CALCULATE FOR EACH SENSOR UNIT AND EACH PARTICLE SIZE RANGE]

$$V_A = \frac{V_T \times AUC_T}{AUC_A}$$

$V_A$ = VOLUMETRIC AIRFLOW (PER SENSOR UNIT)
$V_T$ = TARGET VOLUMETRIC AIRFLOW (PER SENSOR UNIT)
$AUC_T$ = AREA UNDER THE TARGET DECAY CURVE
$AUC_A$ = AREA UNDER THE DECAY CURVE

AVERAGE VOLUMETRIC AIRFLOW, $V_{A,avg}$

[CALCULATE FOR EACH PARTICLE SIZE (S1, S2, S3) AND EACH SENSOR UNIT]

$$V_{A,Un,avg} = V_{A,Un,S1} \times W_{S1} + V_{A,Un,S2} \times W_{S2} + V_{A,Un,S3} \times W_{S3}$$

$V_{A,Un,avg}$ = ACTUAL VOLUMETRIC AIRFLOW, SENSOR UNIT n, AVERAGED OVER ALL PARTICLE SIZES
$V_{A,Un,S1}$ = ACTUAL VOLUMETRIC AIRFLOW, SENSOR UNIT n, PARTICLES IN FIRST SIZE RANGE (S1)
$W_{S1}$ = PARTICLE SIZE DISTRIBUTION WEIGHTING FOR PARTICLES IN FIRST SIZE RANGE (S1)
$V_{A,Un,S2}$ = ACTUAL VOLUMETRIC AIRFLOW, SENSOR UNIT n, PARTICLES IN SECOND SIZE RANGE (S2)
$W_{S2}$ = PARTICLE SIZE DISTRIBUTION WEIGHTING FOR PARTICLES IN FIRST SIZE RANGE (S2)
$V_{A,Un,S3}$ = ACTUAL VOLUMETRIC AIRFLOW, SENSOR UNIT n, PARTICLES IN THIRD SIZE RANGE (S3)
$W_{S3}$ = PARTICLE SIZE DISTRIBUTION WEIGHTING FOR PARTICLES IN FIRST SIZE RANGE (S3)

TARGET TOTAL VOLUMETRIC AIRFLOW

S140

$$V_{T,avg} = \frac{V_{T,U1} + V_{T,U2} + V_{T,U3} + \cdots + V_{T,Un}}{n}$$

ACTUAL TOTAL VOLUMETRIC AIRFLOW

S150

$$V_{A,avg} = \frac{V_{A,U1,avg} + V_{A,U2,avg} + V_{A,U3,avg} + \cdots + V_{A,Un,avg}}{n}$$

$V_T$ = TARGET TOTAL AVERAGE VOLUMETRIC AIRFLOW
$n$ = NUMBER OF SENSOR UNITS
$V_{A,avg}$ = TOTAL AVERAGE VOLUMETRIC AIRFLOW

TEST OUTCOME:

IF: $V_{A,avg} \geq V_{T,avg}$ = PASS
IF: $V_{A,avg} < V_{T,avg}$ = FAIL

*FIGURE 3C*

TRACER DETECTION SYSTEM AND METHOD FOR CHARACTERIZING EFFECTIVENESS OF AIR REMOVAL IN AN AEROSOL ZONE

CROSS-REFERENCE TO RELATED APPLICATIONS

This application claims the benefit of U.S. Provisional Application No. 63/405,340, filed on 9 Sep. 2022, which is incorporated in its entirety by this reference.

This Application is a continuation-in-part application of U.S. patent application Ser. No. 18/077,185, filed on 7 Dec. 2022, which claims the benefit of U.S. Provisional Application No. 63/405,340, filed on 9 Sep. 2022, U.S. Provisional Application No. 63/355,949, filed on 27 Jun. 2022, U.S. Provisional Application No. 63/329,717, filed on 11 Apr. 2022, U.S. Provisional Application No. 63/286,821, filed on 7 Dec. 2021, U.S. Provisional Application No. 63/286,806, filed on 7 Dec. 2021, and U.S. Provisional Application No. 63/286,815, filed on 7 Dec. 2021, each of which is incorporated in its entirety by this reference.

This Application is also a continuation-in-part (or "bypass") application of PCT Application No. PCT/US23/32351, filed on 8 Sep. 2023, which claims priority to U.S. Provisional Application No. 63/405,340, filed on 9 Sep. 2022, and U.S. patent application Ser. No. 18/077,185, filed on 7 Dec. 2022, each of which is incorporated in its entirety by this reference.

TECHNICAL FIELD

This invention relates generally to the field of metagenomics and more specifically to a new and useful system and method for characterizing air-removal effectiveness in an aerosol zone in the field of metagenomics.

BRIEF DESCRIPTION OF THE FIGURES

FIGS. 3A, 3B, and 3C are flowchart representations of the method;

DESCRIPTION OF THE EMBODIMENTS

Figure 1:
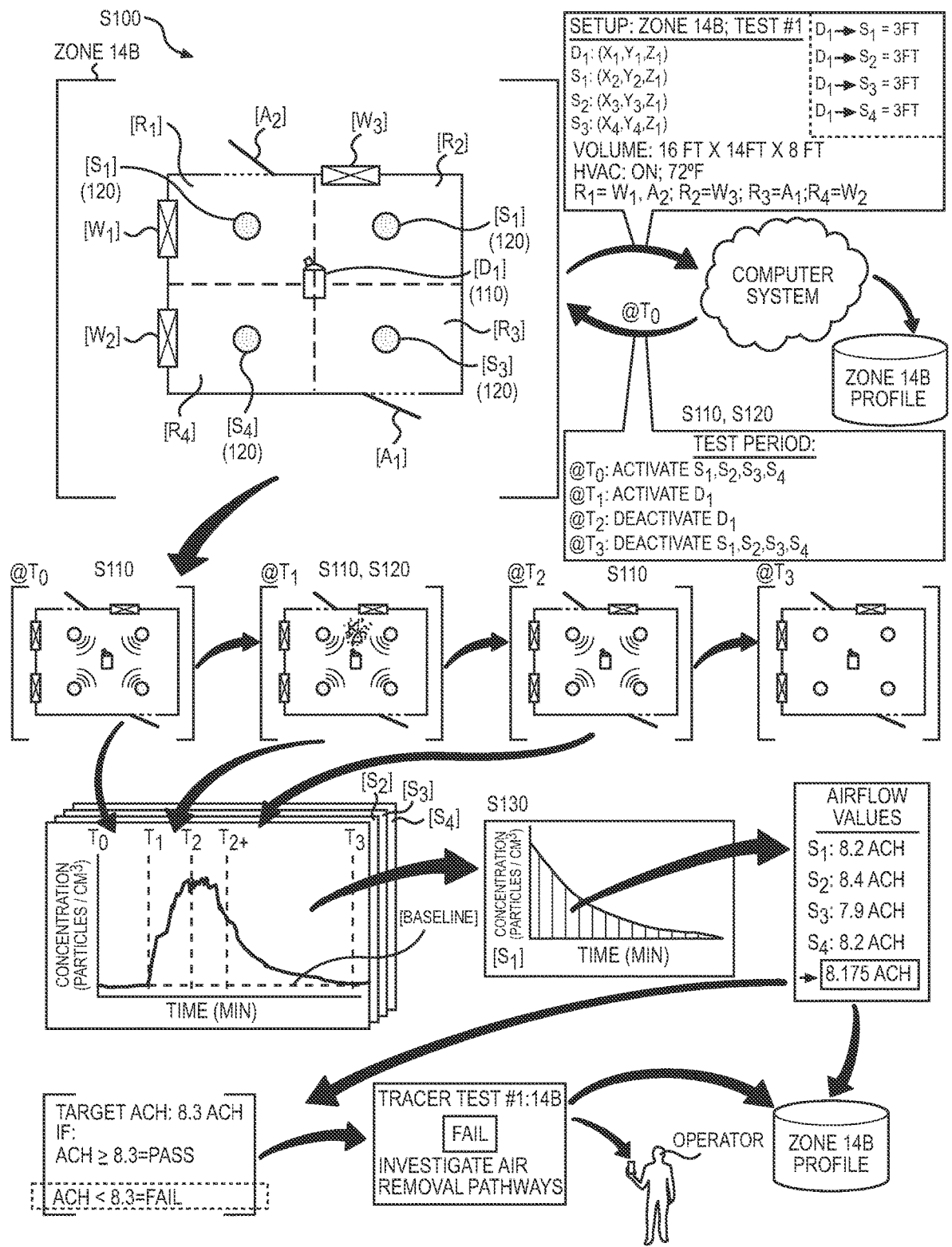
FIG. 1 is a flowchart representation of a method.
Figure 2A:
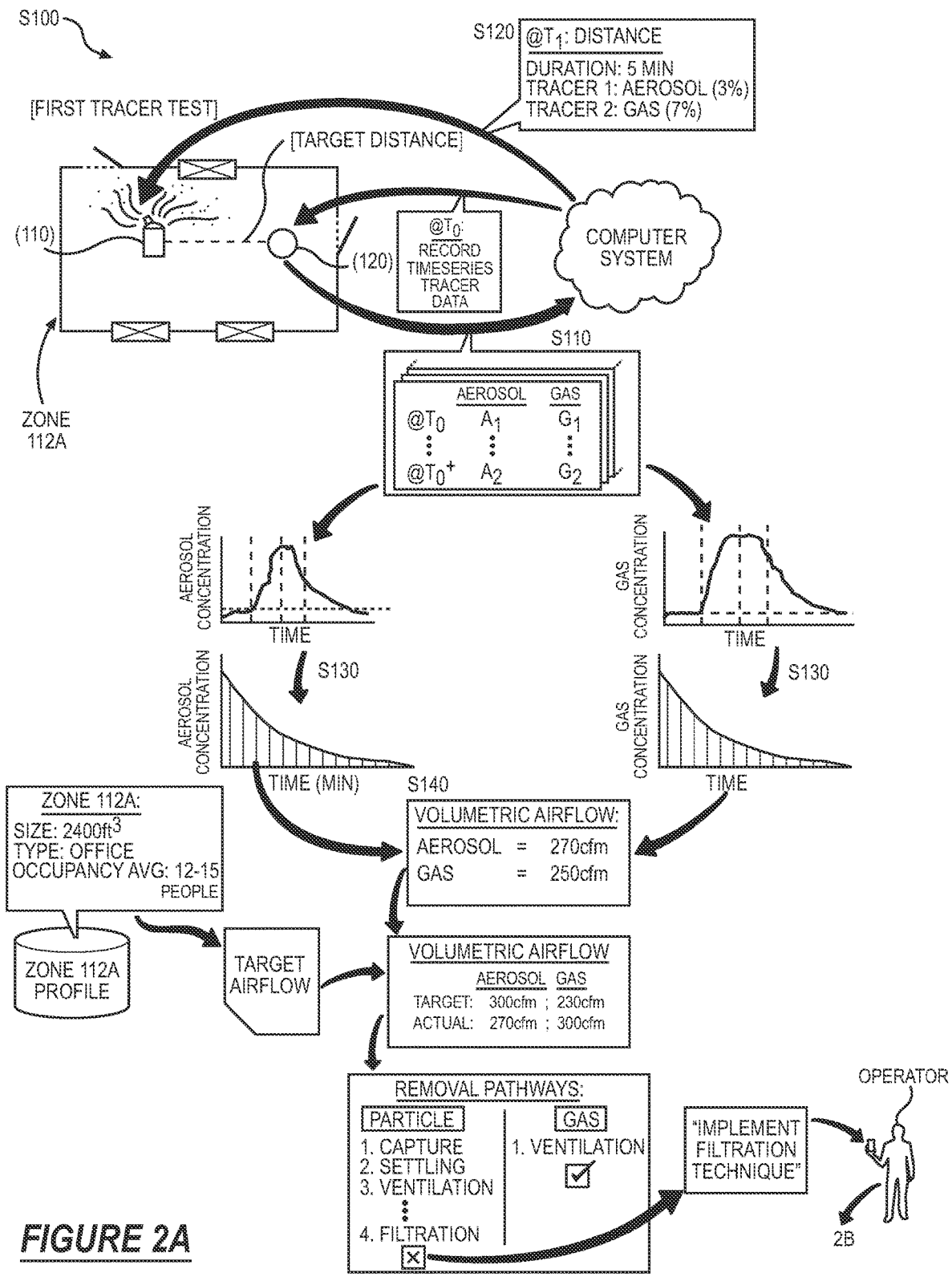
FIGS. 2A and 2B are flowchart representations of the method.
Figure 2B:
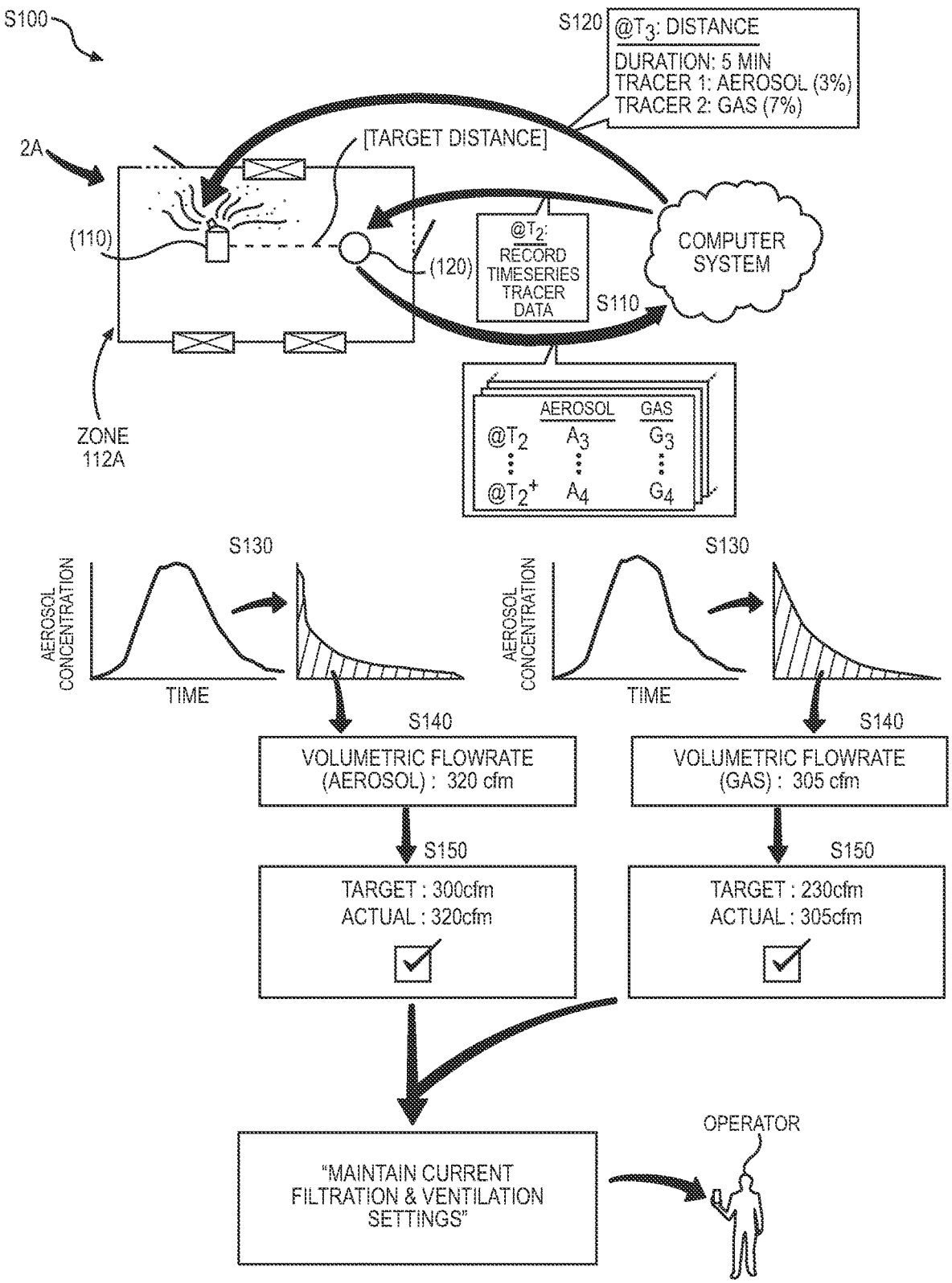

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method: Aerosol Tracer Particles

As shown in FIGS. 1, 2A, 2B, 3A, 3B, 3C, and 4, a method S100 includes, during execution of a first tracer test in an aerosol zone within a first test period: recording a first timeseries of aerosol data via a set of sensors 122 integrated in a first sensor unit 120 transiently arranged in a first unit location in the aerosol zone in Block S110, the first timeseries of aerosol data representing concentrations of aerosol particles present in air at the first unit location during the first test period; and, during a first dispense period, triggering release of a first tracer load into air in the aerosol zone by a dispenser no transiently arranged in a dispenser no location—offset the first unit location by a target distance—in the aerosol zone, the first tracer load including a test concentration of aerosol tracer particles in Block S120. The method S100 further includes: based on the first timeseries of aerosol data and the test concentration, deriving a first tracer concentration curve representing change in concentration of aerosol tracer particles at the first unit location during the first test period in Block S130; based on characteristics of the first tracer concentration curve, deriving a first airflow value representing removal of aerosol particles from the aerosol zone during the first test period in Block S140; and interpreting a first outcome for the first tracer test based on a difference between the first airflow value and a target airflow value defined for the aerosol zone.

In one variation, the method S100 further includes, in response to the first outcome corresponding to a target outcome (e.g., a "pass" outcome, at least a threshold score), verifying a first set of removal pathways (e.g., particle capture, particle settling, ventilation) employed in the aerosol zone during the first test period. Additionally or alternatively, in another variation, the method S100 further includes, in response to the first outcome differing from the target outcome, withholding verification of the first set of removal pathways employed in the aerosol zone.

1.1 Method: Aerosol Tracer Particles+Tracer Gas

As shown in FIGS. 2A-2B, 3A-3C, and 4, one variation of the method S100 includes, during execution of a first tracer test in an aerosol zone within a first test period: during a first dispense period, releasing a first tracer load into air in the aerosol zone via a dispenser no transiently arranged in a target location in the aerosol zone, the first tracer load including a first concentration of aerosol tracer particles and a second concentration of tracer gas; recording a first timeseries of aerosol data via a first sensor transiently arranged in a first location in the aerosol zone, the first timeseries of aerosol data representing presence of aerosol particles in air at the first sensor during the test period; and recording a second timeseries of gas data via a second sensor transiently arranged in a second location in the aerosol zone, the second timeseries of gas data representing presence of tracer gas in air at the second sensor during the test period. In this variation, the method S100 further includes: based on the first timeseries of aerosol data and the first concentration, deriving an aerosol tracer concentration curve representing timeseries concentrations of aerosol tracer particles in the aerosol zone during the test period; based on characteristics of the aerosol concentration curve, characterizing a first airflow value representative of airborne particle removal from the aerosol zone; based on the second timeseries of gas data and the second concentration, interpreting a gas tracer concentration curve representing timeseries concentrations of tracer gas in the aerosol zone during the test period; and, based on characteristics of the gas concentration curve, deriving a second airflow value representative of gas removal from the aerosol zone.

2. Tracer Detection System: Particle Sensor+Gas Sensor

Figure 4:
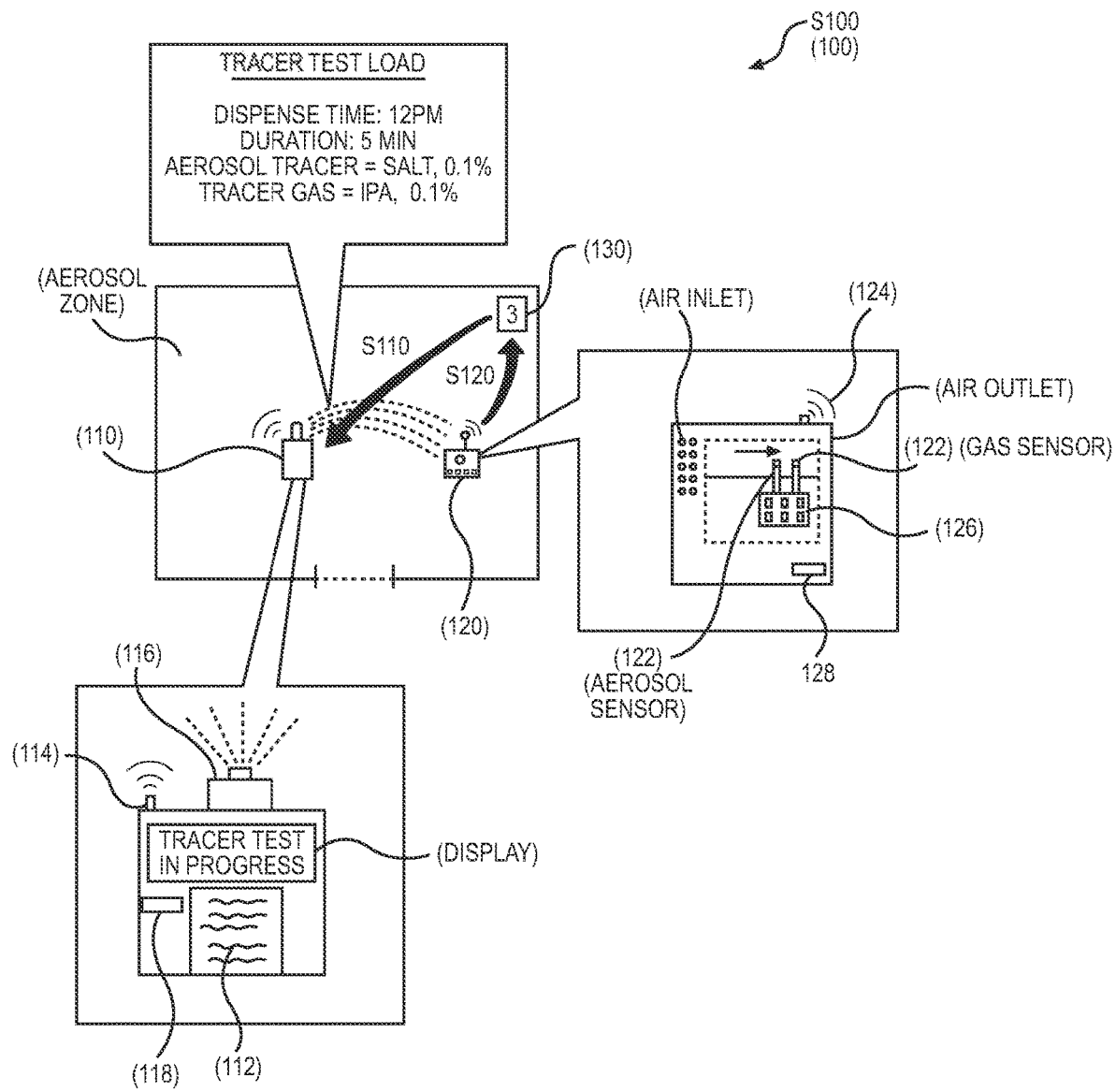
FIG. 4 is a flowchart representation of the method.
Figure 5A:
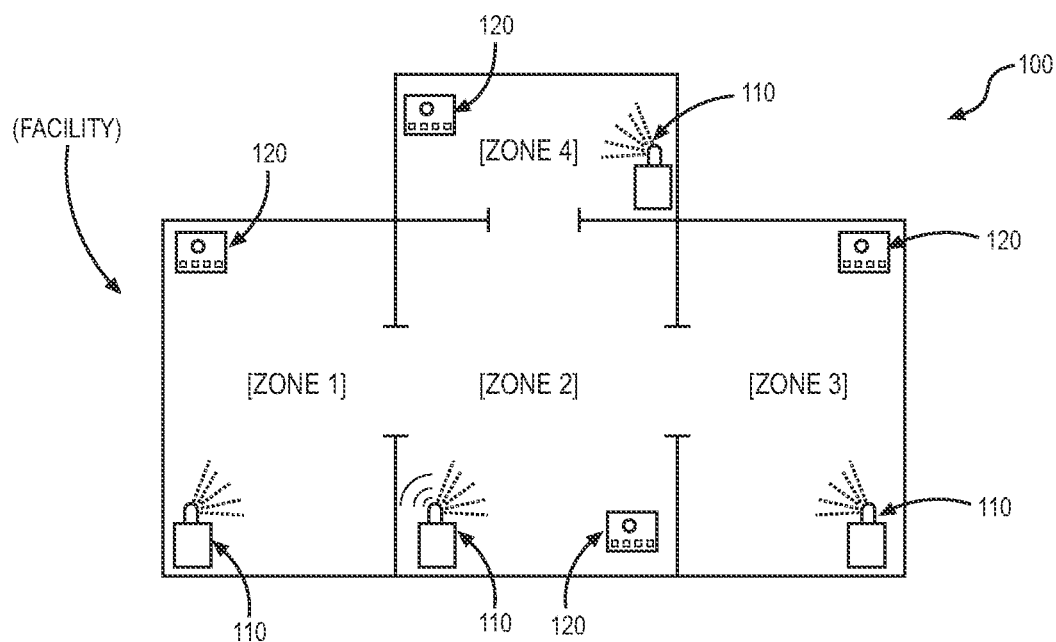
FIGS. 5A and 5B are schematic representation of a system.
Figure 5B:
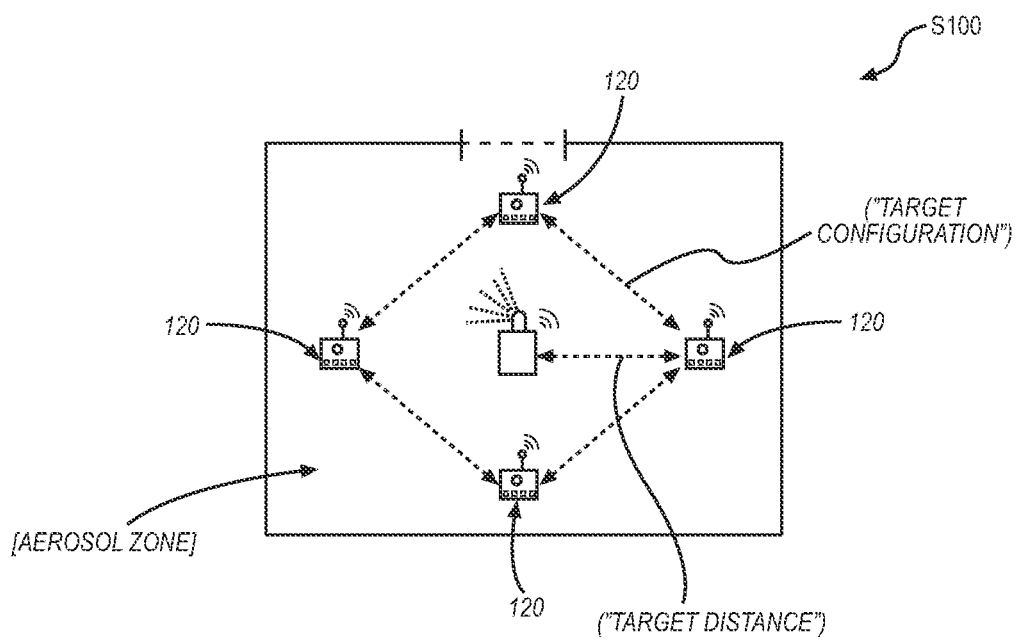

As shown in FIGS. 4, 5A, and 5B, a tracer detection system 100 includes a dispenser 110 transiently installed in a dispenser 110 location in an aerosol zone and including a reservoir 112 containing a mixture of nonvolatile tracers and volatile tracers in solution; an actuator 116 configured to release a tracer test load from the reservoir 112 and into the aerosol zone, the tracer test load including a first concentration of aerosol tracers and a second concentration of a tracer gas; and a first power module 118 configured to supply power to the actuator 116.

The tracer detection system 100 further includes a first sensor unit 120 arranged in a first unit location—offset the dispenser 110 location by a target distance—in the aerosol zone and including a first set of sensors 122; a sensor communication module 124; a controller 124; and a second power module 128 configured to transiently supply power to the first set of sensors 122, the controller 124, and the sensor communication module 124. The first set of sensors 122 includes: a first particle sensor configured to signal presence of aerosol particles in air at the first unit location; and a first gas sensor configured to signal presence of the tracer gas in air at the first unit location. The controller 124 is configured to: read a first timeseries of signals from the first particle sensor responsive to a command received by the sensor communication module 124; read a second timeseries of signals from the gas sensor responsive to the command; interpret timeseries amounts of aerosol particles in air flowing through the first unit location based on the first timeseries of signals; and interpret timeseries amounts of the tracer gas in air flowing through the first unit location based on the second timeseries of signals.

In one variation, the tracer detection system 100 further includes a computer module 130 (e.g., a computer system) configured to: transmit commands to the sensor communication module 124 to selectively trigger recording of timeseries tracer data via the set of sensors 122 integrated within the sensor unit 120; and convert timeseries tracer data recorded by the controller 124 to a set of airflow values representative of airflow in the aerosol zone during execution of a tracer test.

In one variation, the tracer detection system 100 further includes a second sensor unit 120 arranged in a second unit location in the aerosol zone and including: a second set of sensors 122 including a second particle sensor—configured to signal presence of aerosol particles in air at the second unit location—and a second gas sensor configured to signal presence of the tracer gas in air at the second unit location; a second sensor communication module 124; a second controller 124; and a third power module 128 configured to supply power to the second controller 124 and the second set of sensors 122. The second controller 124 is configured to: read a third timeseries of signals from the second particle sensor responsive to a command received by the second sensor communication module 124; read a fourth timeseries of signals from the second gas sensor responsive to the command received by the second sensor communication module 124; interpret timeseries amounts of aerosol particles in air flowing through the second unit location based on the third timeseries of signals; and interpret timeseries amounts of the tracer gas in air flowing through the second unit location based on the fourth timeseries of signals. In this variation, the first sensor unit 120 and the second sensor unit 120 cooperate to define a target arrangement of sensor units 120 arranged about the dispenser 110.

3. Applications

Generally, Blocks of the method S100 can be executed by a computer system (e.g., a local or remote computer system, a computer network, a local or remote server) in conjunction with a tracer detection system 100—including a dispenser 110 and a sensor unit 120—(hereinafter the "system") to: dispense known concentrations of tracers (e.g., aerosolized tracer particles, volatile tracers) in solution into a defined, indoor environment (or "aerosol zone") via a dispenser 110 transiently installed in a dispenser no location within the indoor environment; concurrently capture timeseries tracer data—representing concentrations of tracers in air—via a set of sensor units 120 transiently arranged about the dispenser no in a target configuration; and derive timeseries concentrations—represented by a tracer concentration curve—of these tracers in the indoor environment over time, such as following dispensation of tracers into the indoor environment by the dispenser no. The computer system can then leverage this tracer concentration curve to derive insights related to flow and/or removal of air—including gases and/or particles—in this particular environment.

In one implementation, the tracer detection system 100 can be transiently deployed to a particular facility—such as an office building, a home, a restaurant, a classroom, a shopping mall, a hospital, an airport terminal, etc.—and configured to: dispense known amounts of tracers (e.g., salt particles) into the facility via release of tracer test loads at the molecular tracer dispenser no; and detect amounts of aerosol particles—including aerosolized tracers—in ambient air in the facility at the sensor unit 120. In this implementation, the dispenser 110 can be configured to execute a tracer release according to a particular set of release parameters—such as including a particular dispense time (e.g., a timestamp, a time period), a total duration of the tracer release, a target frequency for each dispensation of tracers during the tracer release, an amount of tracers (e.g., salt) released in each dispensation, etc.—in order to generate a detectable tracer signal configured to enable linking of tracers detected at the sensor unit 120 to tracers dispensed during this particular tracer release. The sensor unit 120—including a set of sensors 122 (e.g., an aerosol particle counter, a gas sensor) configured to detect presence of aerosols in air—can be configured to then record a timeseries of aerosol data representing timestamped amounts of aerosol particles (e.g., aerosolized tracers) detected in air at the sensor unit 120 following execution of the tracer release. The system can then leverage the timeseries of aerosol data, in combination with the known release parameters, to interpret a tracer signal (e.g., a curve or model) representing change in amount of tracers of the tracer type detected at the sensor unit 120 over time following dispensation of the tracer test load. Based on characteristics of this tracer signal, the system can then derive a set of airflow values—such as an air-change rate (e.g., a volumetric air-change rate) and/or an exposure reduction rate—representing flow of aerosol in this particular space.

In particular, during a test period, the system can execute a tracer test to derive insights related to aerosol behaviors—such as related to flow, movement, and/or distribution patterns—in a particular aerosol zone within a facility. In preparation for execution of a tracer test, the aerosol detection system 100 can be deployed to a facility for installation within a particular aerosol zone and/or throughout a group of aerosol zones within the facility. In one implementation, the aerosol detection system 100—such as including one dispenser 110 and one or more sensor units 120—can be transiently deployed and installed within the aerosol zone for a defined duration (e.g., 10 minutes, 30 minutes, 1 hour, 24 hours) to enable execution of a tracer or a series of tracer tests during this defined duration. Once installed in the aerosol zone, the system can execute a tracer test accordingly and interpret a set of airflow values for the aerosol zone based on timeseries aerosol data recorded during execution of the tracer test. The aerosol detection system 100 can then be retrieved from the aerosol zone—such as for installation in another aerosol zone within the facility and/or for storage elsewhere—upon completion of the tracer test or series of tracer tests.

For example, an operator affiliated with the aerosol zone may locate the dispenser no and the sensor unit 120 in the aerosol zone (e.g., a in a target configuration) in preparation for execution of a tracer test. Once deployed within the aerosol zone, the system can: initiate a test period of a target duration (e.g., 10 minutes, 30 minutes, 1 hour, 24 hours); execute one or more tracer tests—including release of a tracer test load by the dispenser no and recording of timeseries aerosol data by the sensor unit 120—within this test period; and, in (near) real-time, output results—such as aerosol metrics (e.g., air-change range, aerosol reduction rate, air velocity and/or direction), risk levels associated with one or more pathogens, effectiveness of various interventions or environmental controls (e.g., HVAC settings, occupancy levels, activity levels)—of each tracer test; and report these aerosol metrics and/or additional insights to a manager affiliated with the aerosol zone in (near) real-time. The system can therefore derive deep insights into flow and movement of aerosols in the aerosol zone via execution of a (relatively) brief tracer test (e.g., a 10-minute test, 20-minute test, 1-hour test).

Figure 3B:
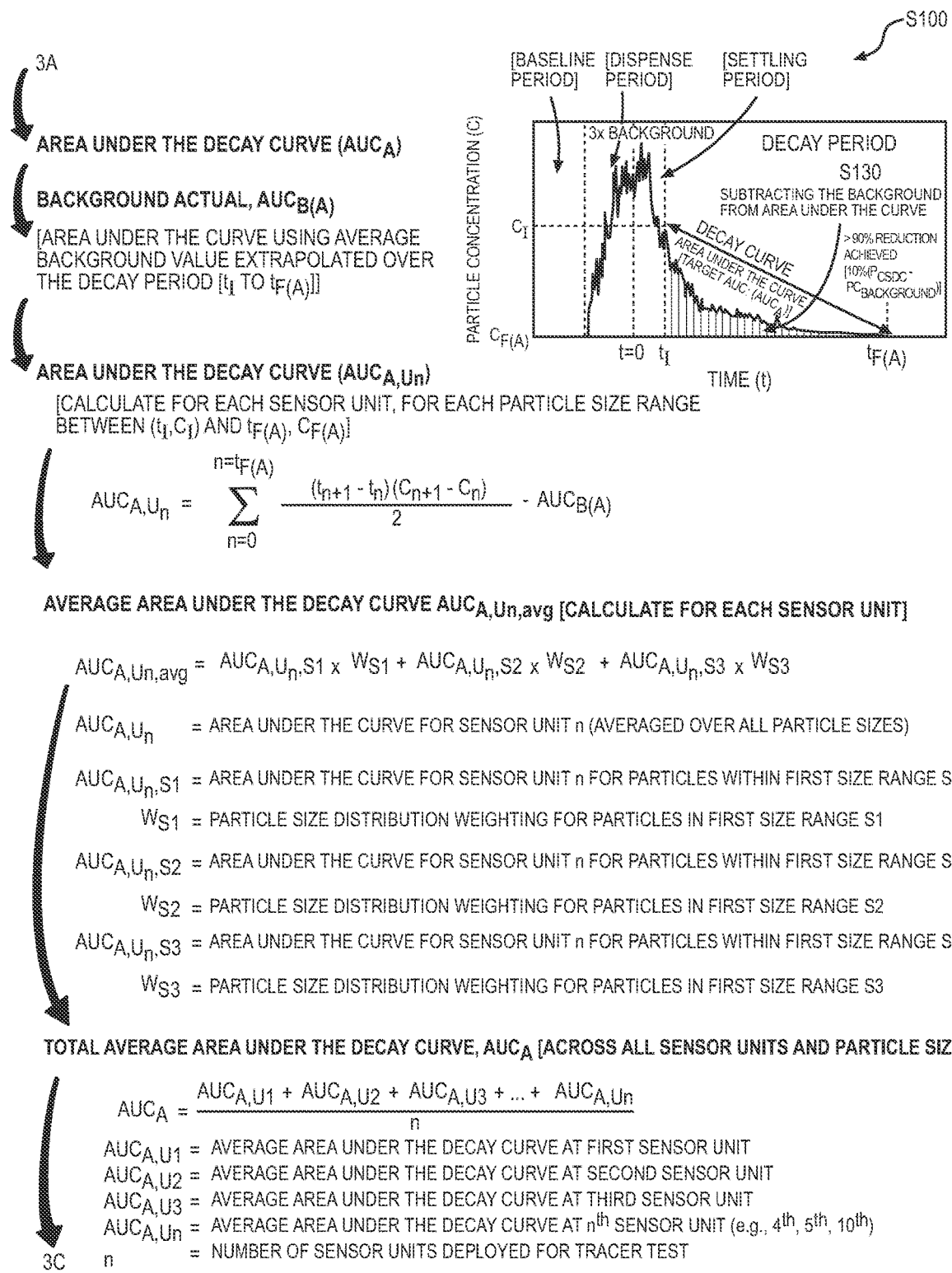

For example, as shown in FIGS. 3A-3C, the system can: derive a tracer concentration curve—representing decay in concentration of a tracer in air in the aerosol zone over a decay period succeeding dispensation of a tracer test load into the aerosol zone—based on timeseries aerosol data captured by one or more sensor units 120 deployed in the aerosol zone during execution of the tracer test; and extract characteristics from this concentration curve—such as including an area-under-the-curve (or "AUC"), a maximum concentration of tracers, a final concentration of tracers, a baseline concentration of tracers in the aerosol zone, a decay rate (e.g., a slope of the cure), etc.—to derive an airflow value (e.g., a volumetric airflow rate) representing removal of tracer particles from the aerosol zone during the tracer test. Furthermore, the system can: compare this airflow value to a target airflow value—such as a target removal rate and/or target air-change rate (e.g., a target volumetric airflow rate)—defined for the aerosol zone; and interpret an outcome—such as a "pass" outcome or a "fail" outcome—of the tracer test based on a difference between the target airflow value and the (measured) airflow value. Based on the outcome, the system can selectively suggest implementation and/or modification of various removal pathways—such as related to capture, filtering, settling, ventilation, etc.—employed in the aerosol zone.

Furthermore, in one variation, the system can leverage different dispensation and detection of tracers of different types to derive insights related to different types of air removal methods employed in the aerosol zone. In particular, the system can: dispense tracer test loads including known concentrations of aerosol tracers (e.g., salt) and tracer gas (e.g., IPA) via the dispenser 110; record timeseries aerosol data—representing concentrations of aerosols over time—via a set of aerosol sensors 122 integrated into one or more sensor units 120 arranged about the dispenser 110 in a target configuration; record timeseries gas data—representing concentrations of the tracer gas over time—via a set of gas sensors 122 integrated into one or more sensor units 120 arranged about the dispenser no; interpret an aerosol concentration curve—and thus derive an aerosol airflow value (e.g., based on characteristics of this aerosol concentration curve) representative of airborne particle removal from the aerosol zone—based on the timeseries of aerosol data; and interpret a gas concentration curve—and thus derive a gas airflow value (e.g., based on characteristics of this gas concentration curve) representative of gas removal from the aerosol zone—based on the timeseries of gas data.

The system can thus: leverage the aerosol airflow value (e.g., a first volumetric airflow) to derive insights related to particle removal pathways (e.g., ventilation, settling, capture) associated with particle and/or aerosol removal in the aerosol zone; and leverage the gas airflow value (e.g., a second volumetric airflow) to derive insights related to gas removal pathways (e.g., ventilation, settling, capture) associated with gas removal from the aerosol zone. The system can therefore: verify gas removal pathways—such as related to ventilation and/or outdoor-air circulation within the indoor environment—independently of particle removal pathways, such as including ventilation and/or outdoor-air circulation, settling, filtering, diluting, etc.; and selectively suggest modifications to each of these removal pathways to improve air removal, minimize costs associated with air removal, and meet and/or exceed target particle and/or gas airflow values defined for the aerosol zone.

4. Tracer Detection System

Generally, the tracer detection system 100 includes a set of tracer dispensers 110 and a set of sensor units 120 transiently deployed within a facility for execution of one or more tracer tests. In particular, the tracer detection system 100 can include: a set of tracer dispensers 110 (e.g., one or more tracer dispensers 110) configured to release known amounts (e.g., quantities, concentrations, volumes) of tracers in solution (i.e., tracer test loads) into air in a defined, indoor environment (hereinafter an "aerosol zone") containing the set of tracer dispensers 110; and a set of sensor units 120 (e.g., one or more sensor units 120) configured to detect tracers in air at the set of sensor units 120 and record timeseries amounts of these tracers.

More specifically, the tracer detection system 100 can include a set of tracer dispensers 110 and a set of sensor units 120 deployed within an aerosol zone, such as within a singular, defined aerosol zone (e.g., an office, a classroom, a kitchen, a hallway) and/or across multiple zones (e.g., a suite of offices, a floor of a building, adjacent classrooms, multiple shops within a shopping mall). Each tracer dispenser 110, in the set of tracer dispensers no, can be configured to periodically release known amounts of tracers (i.e., tracer test loads) into surrounding ambient air; and each sensor unit 120, in the set of sensor units 120, can be configured to ingest surrounding ambient air and detect presence of tracers (e.g., aerosolized tracer particles, tracer gases)—such as including aerosolized tracer particles (or "aerosol tracers") and/or tracer gases released by the set of tracer dispensers 110—present in ingested ambient air via a set of sensors 122 (e.g., a particle or aerosol sensor, a gas sensor) integrated within the sensor unit 120.

Furthermore, the tracer detection system 100 includes (or is connected to) a computer system—such as a local computer system (e.g., a local server or controller 124) located within the facility or a remote computer system (e.g., a computer network)—and connected to the set of tracer dispensers no and/or set of sensor units 120 via a wired or wireless connection. The computer system can be configured to interface with the set of tracer dispensers no and the set of sensor units 120 to execute Blocks of the method S100. For example, the computer system can: selectively activate a tracer dispenser 110, in the set of tracer dispensers no, to trigger release of a tracer test load; and selectively activate a sensor unit 120, in the set of sensor units 120, to trigger the set of sensors 122 to capture timeseries amounts of aerosols in air passing through the sensor unit 120.

In one variation, the tracer detection system 100 can further include a display—such as integrated into the tracer dispenser 110 and/or one or more sensor units 120—configured to render results, prompts, and/or statuses (e.g., generated by the computer system). For example, the tracer dispenser 110 can include a display configured to: indicate a current status of the tracer dispenser 110, such as during, immediately-preceding, immediately-succeeding, and/or in-between execution of tracer releases; render instructions for a user corresponding to the current status; render a set of airflow values—such as a current air-change rate, a current aerosol clearance rate, a current exposure reduction rate, a current infection exposure risk, a current composite risk score—derived by the computer system for a preceding tracer release; render prompts to modify and/or regulate environmental controls in the space; and/or render prompts to modify and/or regulate ventilation systems in the space.

Additionally and/or alternatively, in another variation, the tracer detection system 100 can interface with a user portal (e.g., a native application, a web application) executing on a user computing device—such as a smartphone, a tablet, a desktop computer, etc.—to communicate results, prompts, and/or system statuses to a user or group of users affiliated with the facility.

In one variation, the tracer detection system 100 can include a set of airflow regulators—such as deployed proximal, coupled to, or integrated into a tracer dispenser no and/or sensor unit 120—configured to regulate flow of aerosolized tracers in the environment. For example, the tracer detection system 100 can include a fan proximal and/or integrated into the tracer dispenser 110 and configured to direct flow of aerosolized tracers—released by the tracer dispenser 110—in a particular direction, such as upward into an airstream and/or toward a particular sensor unit 120 or space within a facility containing the tracer dispenser 110. Additionally and/or alternatively, in another example, the tracer detection system 100 can include a fan proximal and/or integrated into the sensor unit 120 and configured to: direct flow of aerosolized tracers in air toward an inlet of the sensor unit 120; and/or promote mixing of aerosols in air surrounding the sensor unit 120.

Furthermore, in one implementation, the sensor unit 120 and the tracer dispenser 110 can be configured to wirelessly communicate with one another. For example, the tracer dispenser 110 can be configured to automatically trigger the sensor unit 120 to initiate recording of timeseries tracer data via the set of sensors 122—such as in preparation for or responsive to dispensation of a tracer test load—responsive to receiving a command from the computer system. Additionally and/or alternatively, in another example, the sensor unit 120 can be configured to automatically trigger the tracer dispenser 110 to dispense a tracer test load—in preparation or responsive to initiating capture of aerosol data by the set of sensors 122—responsive to receiving a command from the computer system and/or based on a dispense schedule or protocol loaded onto a (local) controller 124 of the sensor unit 120.

4.1 Tracer Dispenser

The tracer detection system 100 can include one or more tracer dispensers 110 configured to transiently install within an aerosol zone to dispense known amounts of tracers (e.g., salt, volatile organic compounds, fluorescent material, genetic material) into air in the aerosol zone.

Generally, a tracer dispenser 110 (hereinafter a "dispenser no") can include: a reservoir 112 configured to store tracers in solution; an outlet fluidly coupled to the reservoir 112; and an actuator 116 configured to dispense tracer test loads from the reservoir 112 and through the outlet for release into the aerosol zone. The dispenser 110 can also include a dispenser power supply 118 (e.g., a battery pack, an external power supply) configured to transiently supply power to the actuator 116 for dispensation of tracer test loads from the reservoir 112.

The dispenser 110 can be configured to output a tracer test load of a known volume and including a known concentration of tracers, such that the system can compare a detected tracer level (e.g., tracer quantity, tracer concentration) to a real tracer level (e.g., based on the known volume and the known concentration) in the tracer test load released by the dispenser no. Further, the dispenser no can be configured to intermittently release tracer test loads into the space, such as at a target frequency and/or aligned with collection of air samples by the sensor unit 120. The system can then leverage these tracers as markers in air samples ingested by the sensor unit 120. In particular, the dispenser 110 can be configured to output a set of tracers configured to mimic flow, distribution, and/or dissipation of pathogens (e.g., output in human saliva) in the space. For example, the dispenser no can be configured to output a set of tracers, each tracer in the set of tracers configured to mimic a particular pathogen, in a set of pathogens, detectable in the space. In one example, a tracer test load can include: a first tracer exhibiting sizes (e.g., relatively small sizes) within a first size range matched to pathogens exhibiting sizes within the first size range; and a second tracer exhibiting sizes (e.g., relatively large sizes) within a second size range matched to pathogens exhibiting sizes within the second size range; and a third tracer exhibiting sizes (e.g., relatively moderate sizes) within a third size range between the first and second size range. Therefore, the system can leverage detection of these tracers—which can exhibit different flow or distribution patterns within a space based on their sizes—to better predict flow or distribution of pathogens of different sizes within the space.

In one implementation, the dispenser 110 is configured to receive a replaceable cartridge (i.e., the reservoir 112)—loaded with a set of tracer samples (e.g., highly-concentrated tracer samples)—to dispense particular tracers, contained in the set of tracer samples in the cartridge, into the space. Over time, this cartridge can be replaced to replenish a supply of tracer samples available for dispensation by the dispenser 110 and/or to supply the dispenser 110 with different types of tracer samples.

In one example, the dispenser no can include: a cartridge receptacle; a loading vessel configured to prepare a tracer test load—including a known concentration of tracers in a known volume of an aqueous solution (e.g., a salt-water solution); a fluid reservoir 112 configured to supply metered volumes of the aqueous solution to the loading vessel; and a sprayer (e.g., a nebulizer) fluidly coupled to the loading vessel and configured to release (airborne) aerosolized droplets of the tracer test load into air in the space. In this implementation, the dispenser no can be configured to receive a replaceable (e.g., disposable) cartridge including: an array of tracer reservoir 112S, each tracer reservoir 112 (e.g., a blister reservoir 112, a capsule, a compartment) loaded with a low-volume, highly-concentrated tracer test load including tracers of particular sizes (e.g., within a narrow size range and/or a variety of sizes), concentrations, and/or identities (e.g., genetic identities); and a connector configured to transiently engage the cartridge receptacle and locate the array of tracer reservoir 112S within the dispenser no. The dispenser 110 can then selectively release one or more tracer test loads into the loading vessel for combination with a volume of the aqueous solution to generate a tracer test load exhibiting a particular concentration and identity of tracers. The dispenser 110 can then release this tracer test load into the space via the sprayer. Therefore, the dispenser 110 can be configured to regulate and/or track tracer concentration, tracer identity, and/or tracer size of tracer test loads dispensed.

In one implementation, the dispenser 110 is configured to dispense tracer test loads including known concentrations of salt in solution. In another implementation, the dispenser 110 is configured to dispense tracer test loads including known concentrations of a volatile organic compound (e.g., IPA) in solution. In another implementation, the dispenser no is configured to dispense tracer test loads including known concentrations of fluorescent material in solution. In yet another implementation, the dispenser 110 is configured to dispense tracer test loads including known concentrations of genetic material (e.g., DNA barcodes) in solution. However, the dispenser 110 can be configured to output tracer test loads including any type of detectable tracer and/or any combination of detectable tracers, such as any tracer particle, liquid tracer, tracer gas, genetic tracer including DNA (e.g., DNA barcodes), fluorescent tracer including fluorescent material, salt, etc.

In one variation, the dispenser can further include a dispenser communication module 114 configured to receive commands from the computer system. In this variation, the actuator 116 can be configured to transiently release tracer test loads—including aerosolized tracers in solution—from the reservoir 112 and into the indoor environment based on a command received by the dispenser communication module 114.

4.1.1 Tracer Type

Generally, the dispenser 110 can be configured to transiently dispense tracer test loads including known concentrations of tracers (e.g., aerosol tracers, tracer gas).

In one implementation, the dispenser no can be configured to transiently dispense metered volumes of a tracer test load including aerosol tracers (or "aerosolized tracer particles"). In particular, in this implementation, the tracer detection system 100 includes a dispenser no—transiently installed (and/or configured to transiently install) in a dispenser no location in an aerosol zone—including: a reservoir 112 containing—or configured to receive and store—nonvolatile tracers in solution; and an actuator 116 configured to release a tracer test load—including a known or "test" concentration of aerosol tracers (e.g., derived from nonvolatile tracers in solution in the reservoir 112)—from the reservoir 112 and into the aerosol zone (e.g., via an outlet). In particular, in this implementation, the dispenser 110 can be configured to nebulize volumes of nonvolatile tracers in solution—transiently stored in the reservoir 112—for release into surrounding air via the actuator 116. For example, the dispenser no can be configured to: store a volume of a tracer solution including a known concentration of salt particles (e.g., NaCl) in solution; and release metered volumes of aerosolized salt particles into air in the aerosol zone containing the dispenser no.

Additionally or alternatively, in another implementation, the dispenser no can be configured to transiently dispense metered volumes of a tracer test load including tracer gas (or "gaseous tracer particles," or "gas tracers"). In particular, in this implementation, the tracer detection system 100 includes a dispenser no—transiently installed (and/or configured to transiently install) in a dispenser no location in an aerosol zone—including: a reservoir 112 containing—or configured to receive and store—volatile tracers (e.g., a volatile organic compound) in solution; and an actuator 116 configured to release a tracer test load—including a known or "test" concentration of tracer gas (e.g., derived from volatile tracers in solution in the reservoir 112)—from the reservoir 112 and into the aerosol zone (e.g., via an outlet). In particular, in this implementation, the dispenser 110 can be configured to release volumes of volatile tracers in solution—transiently stored in the reservoir 112—for dispensation as tracer gas into surrounding air via the actuator 116. For example, the dispenser 110 can be configured to: store a volume of a tracer solution including a known concentration of volatile tracers (e.g., isopropyl alcohol)—such as including one or more volatile organic compounds—in solution; and release metered volumes of a tracer gas—derived from the tracer solution—into the aerosol zone containing the dispenser no.

Additionally or alternatively, in yet another implementation, the dispenser 110 can be configured to transiently dispense metered volumes of a tracer test load including aerosol tracers and tracer gas. In particular, in this implementation, the tracer detection system 100 includes a dispenser no—transiently installed (and/or configured to transiently install) in a dispenser no location in an aerosol zone—including: a reservoir 112 containing—or configured to receive and store—a mixture of volatile tracers and nonvolatile tracers in solution; and an actuator 116 configured to release a tracer test load—including a first concentration of aerosol tracers and a second concentration of tracer gas—from the reservoir 112 and into the aerosol zone (e.g., via an outlet). In particular, in this implementation, the dispenser no can be configured to release volumes of volatile and nonvolatile tracers in solution—transiently stored in the reservoir 112—for dispensation as aerosol tracers and tracer gas into surrounding air via the actuator 116. For example, the dispenser no can be configured to: store a volume of a tracer solution including a known concentration of salt (e.g., NaCl) and a known concentration of isopropyl alcohol (or "IPA") in solution; and release metered volumes of a tracer test load—including salt aerosols (or "aerosolized salt") and IPA gas at known concentrations—into the aerosol zone containing the dispenser 110.

4.2 Sensor Unit

The tracer detection system 100 can include one or more sensor units 120 transiently arranged within the aerosol zone and configured to detect presence of tracers in air at (e.g., surrounding, ingested by) these sensor units 120.

In one implementation, a sensor unit 120 can include: a set of sensors 122 configured to detect presence of a set of tracers in air flowing over and/or through the sensor unit 120; a sensor communication module 124 configured to receive commands from the computer system, offload timeseries tracer data (e.g., timeseries concentrations of tracers) to the computer system, and/or enable communication (e.g., via Wi-Fi) between the sensor unit 120 and the computer system (e.g., a remote computer system, a local server), each other sensor unit 120 in a network of sensor units 120 deployed in the space, and/or a set of dispensers 110 installed in the aerosol zone; a controller 124 configured to read signals output by the set of sensors 122 and interpret timeseries amounts (e.g., concentrations) of tracers in air at the sensor unit 120 based on these signals; and a power module 128 configured to supply power to the controller 124, the first set of sensors 122, and/or the sensor communication module 124.

Generally, the sensor unit 120 is configured to transiently or semi-permanently install in a particular environment (e.g., an enclosed space within a building), such as mounted on a stand, fixed to a wall, and/or standing on a floor of a particular room. Alternatively, the sensor unit 120 can be coupled with a mobile apparatus (e.g., a manual or autonomously cart, an autonomous aerial vehicle) configured to transport the sensor unit 120 about a space or facility.

Once deployed (e.g., permanently or temporarily installed) in a particular space, the sensor unit 120 can ingest air from the space over time and draw this air over the set of sensors 122 for detection of tracers in air samples collected from the aerosol zone, such as responsive to a command received by the sensor communication module 124 and/or at a target frequency (e.g., once per day, once per hour, once per minute, continuously).

Furthermore, the tracer detection system 100 can include multiple sensor units 120 installed throughout a particular facility (e.g., one per floor in an office building). For example, the system can include a docking station (e.g., a charging docking station) configured to house a set of sensor units 120, such that each sensor unit 120 can be deployed from the docking station to a particular space (e.g., an office, a classroom, a store, a bathroom) within a larger facility (e.g., an office building, a school, a mall, an airport).

In one variation, the sensor unit 120 includes a set of indicators—such as arranged on an exterior (e.g., of a housing) of the sensor unit 120. In this variation, the set of indicators can be configured to signal detection of tracers—such as of a particular tracer type—at the sensor unit 120 during execution of a tracer test. The sensor unit 120 can thus include the set of indicators to signal initial detection of tracers at the sensor unit 120 and/or completion of a tracer test to an operator present in the bioaerosol zone during execution of the tracer test. For example, the sensor unit 120 can include a set of colorimetric sensors configured to output an optical signal representing an amount of tracers of the tracer type detected at the set of colorimetric sensors.

In one implementation, the sensor unit 120 and the dispenser 110 can be configured to wirelessly communicate with one another, such that the dispenser 110 can automatically trigger the sensor unit 120 to initiate recording of timeseries tracer data in preparation for or responsive to dispensation of a tracer test load and/or the sensor unit 120 can trigger the dispenser 110 to dispense a tracer test load in preparation or responsive to collection of an aerosol sample. For example, the dispenser no can include a dispenser communication module 114 configured to receive commands for releasing tracer test loads. Similarly, the sensor unit 120 can include a sampler communication module configured to receive commands for collecting aerosol samples. In this example, the aerosol detection system 100 can include a controller 126 loaded with a control program—received from the computer system—and configured to: selectively trigger the dispenser 110 to release tracer test loads into the environment according to a dispense schedule defined by the control program; and selectively trigger activation of the sensor unit 120 according to the dispense schedule. Additionally or alternatively, in another implementation, an operator may manually trigger initiation of a tracer test, such as by manually triggering dispensation of a tracer test load via the dispenser 110 and/or manually triggering collection of timeseries tracer data via one or more sensor units 120.

4.2.1 Sensor Unit Type

Generally, the sensor unit 120 can be configured to transiently record timeseries tracer data representing concentrations of tracers in air at (e.g., flowing over, about, or through) the sensor unit 120, such as responsive to a command received by the sensor communication module 124 to initiate a tracer test.

In one implementation, the tracer detection system 100 includes a sensor unit 120 configured to sample air from the aerosol zone and detect aerosol particles present in air for recording of timeseries aerosol data representing amounts of aerosols (or "aerosol particles") detected in air at the sensor unit 120, such as over a particular sampling period. In this implementation, the sensor unit 120 (e.g., a particle or aerosol detector) can be configured to draw air from the aerosol zone over a set of aerosol sensors 122 (e.g., a particle sensor) for detection of aerosol particles—including aerosol tracers released into the external environment by the dispenser 110—present in air at the sensor unit 120. In particular, the sensor unit 120 can include a set of aerosol sensors 122 configured to transiently—such as at a fixed or target frequency (e.g., every 100-millisecond interval, every 200-millisecond interval, every 1-second interval) generate signals representing amounts of aerosol particles (e.g., aerosols) present in air ingested by the sensor unit 120. The controller 124 can then: interpret timeseries aerosol data—representing amounts (e.g., concentrations, quantities) of aerosol particles detected in air by the set of aerosol sensors 122—based on signals read from the set of aerosol sensors 122; store this timeseries aerosol data to a local memory 129 (e.g., a buffer); and/or offload timeseries aerosol data—such as continuously in (near) real-time and/or from the local memory 129 at a particular frequency—to the computer system.

In another implementation, the tracer detection system 100 includes a sensor unit 120 configured to sample air from the aerosol zone and detect tracer gas present in air for recording of timeseries gas data representing amounts of tracer gas detected in air at the sensor unit 120. In this implementation, the sensor unit 120 can be configured to draw air from the aerosol zone over a set of gas sensors 122 (e.g., one or more gas sensors 122) for detection of a tracer gas—released into the external environment by the dispenser 110—present in air at the sensor unit 120. In particular, the sensor unit 120 can include a set of gas sensors 122 configured to transiently—such as at a fixed or target frequency (e.g., every wo-millisecond interval, every 200-millisecond interval, every 1-second interval) generate signals representing amounts of the tracer gas present in air ingested by the sensor unit 120. The controller 124 can then interpret timeseries gas data—representing amounts (e.g., concentrations, quantities) of the tracer gas detected in air by the set of gas sensors 122—based on signals read from the set of gas sensors 122.

In yet another implementation, the tracer detection system 100 includes a sensor unit 120 configured to sample air from the aerosol zone and detect both aerosol particles and tracer gas present in air for recording of timeseries tracer data—including timeseries aerosol data and timeseries gas data—representing amounts of aerosol particles and tracer gas detected in air at the sensor unit 120. In this implementation, the sensor unit 120 can be configured to: draw air from the aerosol zone over a set of aerosol sensors 122 (e.g., one or more particle sensors) for detection of aerosol particles present in air at the sensor unit 120; and draw air from the aerosol zone over a set of gas sensors 122 (e.g., one or more gas sensors 122) for detection of the tracer gas present in air at the sensor unit 120. The controller 124 can then: interpret timeseries aerosol data—representing amounts (e.g., concentrations, quantities) of aerosol particles detected in air by the set of aerosol sensors 122—based on signals read from the set of aerosol sensors 122; and interpret timeseries gas data—representing amounts (e.g., concentrations, quantities) of the tracer gas detected in air by the set of gas sensors 122—based on signals read from the set of gas sensors 122.

5. Tracer Detection System Deployment

Generally, the tracer detection system 100 can be transiently deployed to an aerosol zone for execution of a tracer test in this aerosol zone.

In particular, the tracer detection system 100—including a set of dispensers 110 and a set of sensor units 120—can be transiently arranged in a target configuration within a particular aerosol zone (e.g., a room, an office, a hallway) for execution of a tracer test during a test period. During this test period, the system can: trigger release of the tracer test load—containing known amounts of aerosol tracers (e.g., aerosolized salt particles)—into air in the aerosol zone by one or more dispensers 110, in the set of dispensers 110, arranged in the aerosol zone; and record timeseries aerosol data—representing concentrations of aerosol particles in air—via a set of sensors 122 integrated into one or more sensor units 120, in the set of sensor units 120, arranged in the aerosol zone. The system can then leverage this timeseries aerosol data—collected during execution of the aerosol tracer test—to derive insights related to airflow (e.g., removal rate and/or replacement rate, direction(s) of airflow) and/or flow of aerosol tracers (e.g., decay rate, flow direction) in the aerosol zone.

In one implementation, the tracer detection system 100—including one or more dispensers 110 and one or more sensor units 120—can be transiently deployed to and installed within the aerosol zone for a test period of a target duration (e.g., 10 minutes, 30 minutes, 1 hour, 24 hours) for execution of a tracer test and/or a series of tracer tests during the test period. Once installed in the aerosol zone, the system can execute a tracer test accordingly and interpret a set of airflow values for the aerosol zone based on timeseries aerosol data recorded during execution of the tracer test. The tracer detection system 100 can then be retrieved from the aerosol zone—such as for installation in another aerosol zone within the facility and/or for storage elsewhere—upon completion of the tracer test or series of tracer tests.

For example, an operator affiliated with the aerosol zone may locate a dispenser no and a set of sensor units 120 in the aerosol zone (e.g., a in a target configuration) in preparation for execution of a tracer test. Once deployed within the aerosol zone, the system can: initiate a test period of a target duration (e.g., 10 minutes, 30 minutes, 1 hour, 24 hours); execute one or more tracer tests—including release of a tracer test load by the dispenser no and recording of timeseries aerosol data by the sensor unit 120—within this test period; and, in (near) real-time, output results—such as airflow values (e.g., air-change range, aerosol reduction rate, air velocity and/or direction), risk levels associated with one or more pathogens, effectiveness of various interventions or environmental controls (e.g., HVAC settings, occupancy levels, activity levels)—of each tracer test.

In one example, the system can: trigger dispensation of a tracer test load to initiate a tracer test; derive a tracer signal from timeseries aerosol data collected during execution of the tracer test; derive a set of airflow values representing aerosol flow and/or movement in the aerosol zone based on the tracer signal; and report these airflow values and/or additional insights to a manager affiliated with the aerosol zone in (near) real-time. In this example, the system can therefore derive deep insights into flow and movement of aerosols in the aerosol zone via execution of a (relatively) brief tracer test (e.g., a 10-minute test, 20-minute test, 1-hour test).

Alternatively, in another implementation, the tracer detection system 100—such as including a set of dispensers 110 (e.g., one or more dispensers 110) and a set of sensor units 120 (e.g., one or more sensor units 120)—can be deployed to a facility for permanent or semi-permanent installation within one or more aerosol zones within the facility. In this implementation, once initially installed, the system can periodically execute tracer tests in the aerosol zone and/or within the facility as described above, such as based on a dispense schedule (or "test schedule") defined for the facility and/or responsive to detected environmental changes within the facility.

5.1 Tracer Detection System: Configuration

Generally, as described above, the tracer detection system 100 can be setup in a target configuration within an aerosol zone in preparation for execution of a tracer test.

For example, the tracer detection system 100 can be deployed in a target configuration defining: a quantity and/or arrangement—defining a set of dispenser 110 locations—of a set of dispensers 110 (e.g., one or more dispensers no) transiently installed in the aerosol zone for execution of the tracer test; and a quantity and/or arrangement—defining a set of sensor unit 120 locations—of a set of sensor units 120 (e.g., one or more sensor units 120) transiently installed in the aerosol zone for execution of the tracer test.

5.1.1 Tracer Detection System Configuration: 1 Dispenser+1 Sensor Unit

Generally, as described above, the tracer detection system 100 can be deployed in a target configuration within an aerosol zone in preparation for execution of a tracer test.

In one implementation, the tracer detection system 100 includes: a first dispenser 110—configured to transiently dispense tracer test loads containing known concentrations of aerosol tracer particles arranged in a first dispenser 110 location within the aerosol zone; and a first sensor unit 120 arranged in a first unit location within the aerosol zone and configured to transiently capture timeseries aerosol data representing presence of aerosol particles in air at the first dispenser 110 location.

In particular, the first dispenser 110 can be arranged in the first dispenser no location offset the first dispenser 110 location by a distance falling within a target distance range. For example, to install the tracer detection system 100 in preparation for the tracer test, a user (e.g., a human operator) may: locate the first dispenser no in a first dispenser no location (e.g., defined by the computer system and/or manually selected by the operator), such as in a center of the aerosol zone and/or a location predicted to exhibit minimal variations or turbulence in airflow (e.g., relative the aerosol zone); locate the first sensor unit 120 in a first unit location, such as predicted to intersect a flow path of aerosolized tracers released from the first dispenser no; and confirm connection (e.g., wired or wireless) of the first dispenser no and/or first sensor unit 120 to the computer system. The operator may then initiate the tracer test, such as by manually engaging the actuator 116 of the first dispenser no and/or by triggering initiation within a web or native application executing on the user's computing device and connected to the computer system.

In particular, the operator may locate the first sensor unit 120 at the first unit location defining a distance from the first dispenser 110 location within a target distance range (e.g., between 1 foot and 2 feet, between 6 feet and 8 feet, between 1 meter and 2 meters) defined for the aerosol zone. By thus locating the first sensor unit 120 a particular distance—within the target distance range—from the first dispenser 110, the first sensor unit 120 can be configured to ingest and detect aerosolized tracers, released in the tracer test load by the first dispenser 110, exhibiting aerosol velocities within a threshold deviation of air velocity at the first sensor unit 120 and exhibiting relatively high concentrations, thereby: minimizing error in quantification of aerosolized tracers at the first sensor unit 120; and maximizing a signal-to-noise ratio by increasing quantity of aerosolized tracers present at the first sensor unit 120.

For example, the first dispenser no can be configured to release a tracer test load—including aerosolized tracers—into the aerosol zone, such that these aerosolized tracers exhibit an initial aerosol velocity exceeding an air velocity in the aerosol zone. The first sensor unit 120 can therefore be located at least a minimum distance from the first dispenser 110 in order to enable reduction of aerosol velocity prior to detection—such that, at a time of detection, these aerosolized tracers exhibit an aerosol velocity within a threshold deviation of the air—thereby enabling accurate detection of amounts of aerosolized tracers at the first sensor unit 120. Further, in this example, the first sensor unit 120 can be located within a maximum distance from the first dispenser no in order to limit dispersion of aerosolized tracers within the aerosol zone prior to detection at the first sensor unit 120, thereby increasing detectability of these aerosolized tracers at the first sensor unit 120.

Additionally, in order to further increase detectability of aerosolized tracers at the first sensor unit 120, the operator may locate the first sensor unit 120 at the first unit location defining an orientation—relative the first dispenser 110 location—corresponding to a direction of aerosol flow from the first dispenser 110.

In one variation, the user may manually execute a directionality test in the aerosol zone—prior to installing the first sensor unit 120 within the aerosol zone—in order to predict the first unit location for the first sensor unit 120. For example, the user may: locate the first sensor unit 120 in the first unit location; manually trigger release of a tracer test load (e.g., over a shortened dispense period); and visually inspect flow of aerosolized tracers, in the tracer test load, outward from the first dispenser 110 to identify a primary direction and/or pathway of aerosol flow from the first dispenser no. The operator may then locate the first sensor unit 120 at the first unit location intersecting this pathway of aerosol flow from the first dispenser no. By thus locating the first sensor unit 120 along this pathway of aerosol flow, the first sensor unit 120 can be configured to: initially ingest aerosolized tracers, dispensed in the tracer test load, at a minimum duration from initial release of these aerosolized tracers by the first dispenser 110, thereby reducing time to detection following dispensation; and, via the set of sensors 122, detect a maximum amount (e.g., concentration) of aerosolized tracers at an initial time of detection—such as prior to increased dissipation of aerosolized tracers within the aerosol zone—thereby increasing a signal-to-noise ratio of the resulting tracer signal.

5.1.2 Tracer Detection System Configuration: 1 Dispenser+Multiple Sensor Units

Additionally or alternatively, in another implementation, the tracer detection system 100 can include: a first dispenser 110 arranged in a first dispenser no location within the aerosol zone; and a set of sensor units 120 transiently arranged in a set of unit locations—defining a target arrangement about the first dispenser 110—configured to transiently capture timeseries aerosol data representing presence of aerosol particles in air at the set of dispenser no locations.

In particular, in this implementation, the tracer detection system 100 can include: the first dispenser no transiently arranged in the first dispenser no location; a first sensor unit 120 transiently arranged in a first unit location in the aerosol zone; and a second sensor unit 120 transiently arranged in a second unit location in the aerosol zone. Additionally, the tracer detection system 100 can include additional sensor units 120 arranged in the aerosol zone, such as including a third sensor unit 120 transiently arranged in a third unit location in the aerosol zone, a fourth sensor unit 120 transiently arranged in a fourth unit location in the aerosol zone, etc.

In one example, the first dispenser 110 can be arranged in a first dispenser 110 location defining an approximate center of a room, such as within a threshold distance of a center of the room. The set of sensor units 120 can include: a first sensor unit 120 arranged in a first unit location offset the first dispenser 110 location by approximately (e.g., within 5 percent, within 20 percent) a first distance; a second sensor unit 120 arranged in a second unit location offset the first dispenser 110 location by approximately the first distance and offset the first unit location by approximately a second distance; a third sensor unit 120 arranged in a third unit location offset the first dispenser 110 location by approximately the first distance and offset the second unit location by approximately the second distance; and a fourth sensor unit 120 arranged in a fourth unit location offset the first dispenser no location by approximately the first distance, offset the third unit location by approximately the second distance, and offset the first unit location by approximately the second distance.

The first, second, third, and fourth sensor units 120 can therefore be arranged in a square configuration—each sensor unit 120 offset each adjacent sensor unit 120 by approximately the second distance—about the dispenser 110 arranged in the first dispenser no location in the center of the room.

In one variation, the tracer detection system 100 can be arranged in a target configuration defining a quantity of sensor units 120 corresponding to a size (e.g., an area, a volume) of the aerosol zone. For example, the tracer detection system 100 can include a first dispenser 110 and a set of sensor units 120 transiently arranged in a target configuration within an aerosol zone defining a set of discrete regions of approximately equivalent (e.g., within 5 percent, 10 percent, 20 percent) size (e.g., volumetric area, cross-sectional area). In this example, each sensor unit 120, in the set of sensor units 120, can be transiently installed in a particular discrete region, in the set of discrete regions, such that the target configuration defines a quantity of sensor units 120—in the set of sensor units 120—corresponding to a quantity of discrete regions in the set of discrete regions.

5.2 Variation: Target Configuration Calculation

In one variation, the system can: automatically calculate a target configuration for the first sensor unit 120 and the first dispenser 110 within the aerosol zone; and prompt the operator to locate the first sensor unit 120 and the first dispenser no in this target configuration in preparation for a tracer test. For example, the system can: access a set of zone characteristics—such as a set of dimensions, a total volume, a layout, an activity type or types (e.g., office work, exercise, singing, eating) associated with the aerosol zone, etc.—defined for the aerosol zone; access a set of environmental controls (e.g., current and/or historical environmental controls)—such as a current or average occupancy level, duration of human occupancy, a set of HVAC settings and/or ventilation settings, etc.—defined for the aerosol zone; and, based on the target distance range, the set of zone characteristics, and/or the set of environmental controls, calculate a target configuration—defining the first dispenser 110 location and the first unit location—for deployment of the tracer detection system 100 within the aerosol zone.

Additionally and/or alternatively, in this implementation, the system can: calculate the first dispenser no location based on the set of zone characteristics and/or the set of environmental controls; generate a prompt to execute a directionality test in the aerosol zone prior to installing the first sensor unit 120 within the aerosol zone; transmit the prompt to the operator; and, in response to confirming execution of the directionality test, prompt the user to specify a direction of aerosol flow from the first dispenser no. Based on this direction and the first dispenser 110 location, the system can then: calculate the first unit location; generate a prompt to locate the first sensor unit 120 at the first unit location; and transmit the prompt to the operator.

5.2 Variation: Setup Verification

In another variation, the system can verify a setup configuration of the tracer detection system 100 within the aerosol zone prior to execution of a tracer test. For example, the system can: generate a prompt to confirm deployment of a first dispenser 110 and a first sensor unit 120 in the aerosol zone; and transmit the prompt to an operator associated with the aerosol zone, such as via a mobile device (e.g., a smartphone, a tablet) accessed by the operator or via a display connected and/or integrated into the first dispenser no and/or the first sensor unit 120. Then, in response to receiving confirmation of deployment from the operator, the system can: access a first geolocation of the first sensor unit 120 (e.g., via RSS-based localization techniques) within the aerosol zone; access a second geolocation of the dispenser no within the aerosol zone; and calculate a distance between the first geolocation and the second geolocation. Then, in response to the distance falling within a target distance range defined for the aerosol zone, the system can: verify the setup configuration; and enable execution of a tracer test in the aerosol zone. Alternatively, in response to the distance falling outside a target distance range defined for the aerosol zone, the system can: generate a prompt to adjust (e.g., increase or decrease) the distance between the dispenser 110 and the sensor unit 120; and transmit the prompt to the operator. The system can then repeat this process until the distance falls within the target distance range.

5.4 Test Setup Data

In one implementation, the system can access a set of setup data representative of a setup configuration implemented during execution of the tracer test in the aerosol zone. In particular, in this implementation, the system can: access a set of test setup data—such as including dispenser no and/or sensor configuration data, characteristics of the aerosol zone (e.g., a size, an average occupancy level, locations of various objects in the aerosol zone), a set of current HVAC settings employed by an HVAC system installed in the aerosol zone, etc.—captured prior to execution of a tracer test in the aerosol zone; write this set of test setup data to a test data packet generated for this particular tracer test and stored in a zone profile generated for the aerosol zone.

For example, the system can: access a set of zone characteristics defined for the aerosol zone, such as a size (e.g., area, volume, height, width, length), a quantity and/or location of windows, air vents, doorways, etc., a current occupancy level; access an arrangement (or "configuration") of the set of sensor units 120 and/or the set of dispensers no in the aerosol zone, such as defining a location of each dispenser 110 and/or sensor unit 120 in the aerosol zone, a lateral and/or longitudinal distance between each dispenser 110 and each sensor unit 120, a lateral and/or longitudinal distance between a sensor unit 120 and each other sensor unit 120 installed in the aerosol zone; and/or access a set of historical and/or current conditions in the aerosol zone—such as including HVAC settings (e.g., a ventilation rate), occupancy level, activity type (e.g., exercise, work, eating, speaking, singing) assigned to the aerosol zone.

In one example, the system can access an image (e.g., a 2D or 3D image) of the aerosol zone—such as captured via a mobile device accessed by the operator—and extract a set of test setup data based on features detected in the image. Additionally or alternatively, in another example, the system can access a set of laser sensor data—such as captured manually by an operator inspecting the aerosol zone via a laser sensor device and/or by a laser sensor installed on the sensor unit 120 and/or dispenser 110—and extract a set of test setup data based on the set of laser sensor data. Additionally or alternatively, in yet another example, the system can prompt the operator to manually upload a set of setup data defined for the aerosol zone.

6. Tracer Test: Aerosol Data Collection

Block Silo of the method S100 recites: during execution of a first tracer test within a first test period, recording a first timeseries of aerosol data—representing concentrations of aerosol particles present in air at the first unit location during the first test period—via a set of sensors 122 integrated in a first sensor unit 120 transiently arranged in a first unit location in the aerosol zone.

Generally, in Block Silo, the sensor unit 120 can access a set of sensors 122 (e.g., a set of particle sensors) configured to signal presence of aerosol particles in air at the set of sensors 122 and record aerosol data at a series of target time increments. In particular, the computer system can trigger the first sensor unit 120 to: initiate recording of timeseries aerosol data via the set of sensors 122 at a first time during the first test period; and continue recording timeseries aerosol data throughout a remainder of the first test period.

In one implementation, the computer system can return a command to the sensor unit 120—such as via the sensor communication module 124—to begin recording the timeseries of aerosol data via the set of sensors 122. For example, in response to receiving confirmation to initiate the tracer test from the operator (e.g., via the user's mobile device), the computer system can: generate a command to initiate the tracer test; and transmit this command to the sensor unit 120 via the sensor communication module 124. The sensor unit 120 can then: receive the command from the computer system (e.g., via the sensor communication module 124); trigger the set of sensors 122 to begin recording timeseries aerosol data at a fixed sampling frequency (e.g., 100-microsecond intervals, 200-microsecond intervals, 1-second intervals); and offload the timeseries of aerosol data to the computer system, such as in real-time or in intermittent data packets.

In this implementation, the sensor unit 120 can record aerosol data continuously and/or semi-continuously, such as at each 100-millisecond, 200-millisecond, or 1-second interval. Additionally or alternatively, the sensor unit 120 can selectively sample aerosol data intermittently (e.g., once every 1-second interval, once every 5-second interval, once every 30-second interval) to reduce power consumption and minimize data files, such as prior to completion of the dispense period. In each of these implementations, the sensor unit 120 can then transmit the aerosol data to the computer system at a particular logging frequency (e.g., once-per-second, once every 15-second interval, once every 30-second interval).

In particular, the sensor unit 120 can: record a timeseries of aerosol data as described above; write the timeseries of aerosol data to local storage on the sensor unit 120; and upload the aerosol data to the computer system (e.g., via the sensor communication module 124) at a target logging frequency. Generally, the sensor unit 120 can record packets of aerosol data for a fixed duration (e.g., 100 milliseconds, 1 second, 15 seconds, 1 minute); timestamp each packet of aerosol data; and transmit each data packet wirelessly to the computer system. The computer system can then combine a series of data packets received within a particular time window into a single file of aerosol data. The computer system can leverage the timestamp associated with each data packet to assemble a timeseries of data packets representative of timeseries aerosol data collected throughout a duration of the first test period.

6.1 Background Period

In one implementation, at a start of the test period, the computer system can trigger the sensor unit 120 to begin recording timeseries aerosol data during a background period preceding a dispense period corresponding to release of the tracer test load by the dispenser no. The computer system can then leverage this timeseries aerosol data to interpret background or "baseline" levels (e.g., concentrations, quantities) of aerosol particles in the aerosol zone, such as absent aerosol particles added to the aerosol zone via dispensation of the tracer test load.

In this implementation, during the test period, the sensor unit 120 can record a timeseries of aerosol data—representing concentrations of aerosol particles in air—throughout a duration of the test period. In particular, the system can: record a first subset of the timeseries of aerosol data via the set of sensors 122 (e.g., aerosol sensors 122) integrated in the sensor unit 120 during a background period (e.g., within the test period) preceding the dispense period; and derive a baseline concentration of aerosol particles present in the aerosol zone during the first test period based on the first subset of the first timeseries of aerosol data.

The sensor can then continue recording the timeseries of aerosol data throughout the test period to: capture a second subset of the timeseries of aerosol data via the set of sensors 122 during a decay period succeeding the dispense period (e.g., by a target duration); and derive a tracer concentration curve—for the tracer test—based on the second subset of the timeseries of aerosol data and the baseline concentration.

6.2 Dispense Period

Block S120 of the method Sim, recites: during a first dispense period within the first test period, triggering release of a first tracer load into air in the aerosol zone by a dispenser 110 transiently arranged in a dispenser no location—offset the first unit location by a target distance—in the aerosol zone, the first tracer load including a test concentration of aerosol tracer particles.

Generally, the computer system can define a set of release parameters for a particular tracer test and/or for a particular aerosol zone, such as: a duration of a dispense period corresponding to release of the tracer test load; a start time of the dispense period; an end time of the dispense period; an aerosolization rate of tracers dispensed from the reservoir 112 and into ambient air in the aerosol zone; a target ejection force for releasing the tracer test load from the dispenser 110; a target aerosolization jet distance; an amount (e.g., concentration, quantity) of tracers released in the tracer test load; a tracer type (e.g., a size, a reactivity, a class, a particular molecule or particle); etc. The system can then record the set of release parameters implemented for the tracer test for combining with timeseries aerosol data collected during execution of the tracer test. For example, the system can store the set of release parameters for a particular tracer test in a test container, in a set of test containers, corresponding to execution of the particular tracer test in the aerosol zone.

In one implementation, the computer system can return a command to the dispenser 110—such as via a dispenser 110 communication module—to release the tracer test load over a dispense period according to the set of release parameters defined for this particular tracer test and/or this particular aerosol zone. In one example, the computer system can automatically return a command to the dispenser 110 to execute a release of the tracer test load according to the set of release parameters responsive to confirming setup of the aerosol detection system 100 in the aerosol zone. In another example, the computer system can return a command to the dispenser 110 to execute a release of the tracer test load according to the set of release parameters responsive to receiving a request to initiate the tracer test from a user computing device accessed by the operator or any other user affiliated with the aerosol zone or facility containing the aerosol zone.

For example, the dispenser no can include a reservoir 112—such as a replaceable cartridge and/or fixed reservoir 112—loaded with salt particles (e.g., NaCl particles) in solution. To initiate a tracer test, the computer system can return a command to the dispenser 110 communication module to release a tracer test load—including aerosolized salt particles in solution—over a dispense period according to a set of release parameters including a start time of the dispense period (e.g., an initial dispense time) and a duration of the dispense period. Then, at the specified start time, the actuator 116 of the dispenser 110 can aerosolize a metered volume of salt particles in solution—drawn from the reservoir 112—for release into air in the aerosol zone at a particular aerosolization rate over the duration of the dispense period.

Additionally and/or alternatively, in another implementation, the operator may manually select a user control (e.g., a button, a switch) arranged on the dispenser 110 configured to trigger initiation of a tracer test. In this implementation, the computer system can: receive a query for release parameters from the dispenser no; access the set of release parameters defined for the tracer test in the aerosol zone; and return a command to the dispenser 110 to execute a release of the tracer test load according to the set of release parameters. Additionally and/or alternatively, the computer system can preload the set of release parameters onto the dispenser no.

7. Tracer Signal Analysis

Block S130 of the method S100 recites: based on the first timeseries of aerosol data and the test concentration, deriving a first tracer concentration curve representing change in concentration of aerosol tracer particles at the first sensor unit 120 location during the first test period.

Generally, during execution of the tracer test, the system can: access timeseries aerosol data from the sensor unit 120 at a target logging rate, as described above; and record this timeseries aerosol data to a test container, in a set of test containers, generated for the tracer test. Then, the system can: leverage the set of release parameters defined for the tracer test to: identify a target sampling window (or "decay period")— such as defining an initial time and a final time—within the test period corresponding to the tracer signal; and derive the tracer signal—such as represented by a tracer concentration curve—based on timeseries aerosol data collected during this target sampling window.

In particular, the system can: trigger recording of a first timeseries of aerosol data via the set of sensors 122 integrated into the sensor unit 120 over a duration of a test period, the first timeseries of aerosol data representing amounts of aerosolized particles in ambient air ingested by the first sensor unit 120 during the test period; and trigger release of a tracer test load into ambient air in the aerosol zone—over a dispense period within a test period—according to a first set of release parameters including an initial dispense time corresponding to a start of the dispense period, a duration of the dispense period, and/or a dispensation rate representing a rate of release of aerosolized tracers from the dispenser 110 during the test period. Then, in response to completion of the test period, the system can: calculate a target sampling window—defining an initial sampling time and a final sampling time—based on the first set of release parameters; extract a second timeseries of aerosol data—collected during the target sampling window—from the first timeseries of aerosol data; and derive a tracer concentration curve—representing changes in amounts of aerosol tracers in air detected at the sensor unit 120 during the sampling window between the initial sampling time and the final sampling time—based on the second timeseries of aerosol data.

In one implementation, the system can define the target sampling window to align with a period of decay (e.g., exponential decay) in amount of tracers of the tracer type detected at the sensor unit 120. In particular, in this implementation, the system can derive a tracer signal—such as a decay curve representing decrease (e.g., exponential decay) in amount of tracers of the first type over the target sampling window—based on timeseries aerosol data collected by the sensor unit 120 during the target sampling window, such that: the initial sampling time corresponds to a maximum amount (e.g., concentration, quantity) of tracers of the tracer type; and the final sampling time corresponds to a minimum amount or "baseline" amount of tracers of the tracer type. The system can thus derive the tracer signal or "curve" (e.g., a decay curve, a calibration curve) configured to model change in amount (e.g., concentration, quantity) of tracers of the particular tracer type over time throughout the target sampling window. For example, the system can derive an exponential decay curve representing change in amount (e.g., concentration) of tracers of the tracer type over time during the target sampling window.

In one example, the system can: access a baseline amount of tracers of the tracer type defined for the aerosol zone, such as recorded during an initial time period within the test period—prior to the dispense period—and/or derived for the aerosol zone during one or more preceding test periods; at each timepoint represented in the timeseries of bioaerosol data, estimate an amount of tracers, of the tracer type, originating from the tracer test load based on a difference between an amount of tracers recorded at the timepoint and the baseline amount of tracers; identify a maximum amount of tracers of the first tracer type at a first time in the timeseries aerosol data; identify a final amount of tracers—corresponding to the baseline amount and/or within a threshold deviation of the baseline amount—at a second time, succeeding the first time, in the timeseries aerosol data; and select the target sampling window spanning from the first time to the second time. Then, the system can: isolate timeseries of aerosol data collected during the selected sampling window; and leverage statistical models and/or linear regression techniques—such as by implementing a log-linear fit—to derive a tracer decay curve (i.e., a tracer signal) representing or modeling decay in amount of tracers of the tracer type detected by the sensor unit 120 over time, during the sampling window.

In another implementation, the system can: access a set of predefined rules for selection of the target sampling window in the aerosol zone; access the set of release parameters defined for the tracer test; and select the sampling window based on the set of predefined rules and the set of release parameters.

7.1 Background Period+Dispense Period+Release Period+Decay Period

In one implementation, the system can identify discrete subsets of the timeseries of aerosol data—captured by the sensor unit 120—corresponding to different time periods within the test period.

In particular, in this implementation, the system can identify: a first subset of the timeseries of aerosol data corresponding to a background period—spanning between a first time and a second time—preceding dispensation of the tracer test load into the aerosol zone; a second subset of the timeseries of aerosol data corresponding to the dispense period—during which the dispenser no releases the tracer test load into the aerosol zone—succeeding the background period and spanning between the second time and a third time; a third subset of the timeseries of aerosol data corresponding to a settling period—spanning between the third time and a fourth time—succeeding the dispense period and of a target duration (e.g., one minute, five minutes, 15 minutes); and a fourth subset of the timeseries of aerosol data corresponding to a decay period—corresponding to removal of tracer aerosols from the aerosol zone—succeeding the settling period and spanning between the fourth time and a fifth time succeeding the fourth time.

The system can then: derive a baseline concentration of aerosol particles present in the aerosol zone during the first test period based on the first subset of the timeseries of aerosol data captured during the background period; and derive a tracer concentration curve based on the third subset of the timeseries of aerosol data—captured during the decay period—and the baseline concentration. In particular, the system can isolate timeseries data recorded during the decay period—from timeseries aerosol data recorded during the dispense and/or settling periods—to minimize noise in the aerosol data due to fluctuations in aerosol concentrations during and/or immediately succeeding dispensation of the tracer test load as air in the aerosol zone returns to equilibrium.

Furthermore, the system can leverage the derived baseline concentration of aerosol particles to normalize concentrations of aerosol tracers represented in the timeseries of aerosol data, thereby accounting for aerosol particles naturally-present in the aerosol zone.

7.2 Airflow Values

Block S140 of the method S100 recites: based on characteristics of the first tracer concentration curve, deriving a first airflow value representing removal of aerosol particles from the aerosol zone during the first test period. Generally, the system can leverage characteristics of the tracer concentration curve—derived from timeseries aerosol data collected by the sensor unit 120 during the decay period—to derive insights related to airflow and/or flow of tracers (e.g., particle or aerosol tracers, tracer gas) in the aerosol zone.

In one implementation, the system can: extract an area defined by the tracer concentration curve (an area-underthe-curve or "AUC"); and derive a volumetric airflow rate for the aerosol zone based on the area and a known volume of the aerosol zone. In particular, in this implementation, the system can implement the process depicted in FIGS. 3A-3C to derive an airflow value (e.g., an air-change range) representing removal of air—including particles and/or gases—from the aerosol zone.

Additionally, in one implementation, the system can derive a composite airflow value for an aerosol zone based on a set of tracer concertation curves derived from timeseries aerosol data collected at each sensor unit 120, in the set of sensor units 120, arranged about the dispenser 110 in the aerosol zone.

For example, during the test period, the system can: record a first timeseries of aerosol data via a first set of sensors 122 integrated in a first sensor unit 120 transiently arranged in a first unit location in the aerosol zone, the first timeseries of aerosol data representing concentrations of aerosol particles present in air at the first unit location; record a second timeseries of aerosol data via a second set of sensors 122 integrated in a second sensor unit 120 transiently arranged in a second unit location in the aerosol zone, the second timeseries of aerosol data representing concentrations of aerosol particles present in air at the second unit location; and, during a dispense period, trigger release a first tracer load into air in the aerosol zone by a dispenser 110 transiently arranged in a dispenser 110 location in the aerosol zone, the first tracer load including a test concentration of aerosol tracer particles. Then, the system can: based on the first timeseries of aerosol data and the test concentration, derive a first tracer concentration curve representing change in concentration of aerosol tracer particles at the first unit location; based on the second timeseries of aerosol data and the test concentration, derive a second tracer concentration curve representing change in concentration of aerosol tracer particles at the second unit location; and derive a (composite) airflow value representing removal of aerosol particles from the aerosol zone during the first test period based on the first timeseries of aerosol data, the second timeseries of aerosol data, and the test concentration.

7.3 Tracer Test Outcome

Block S150 of the method S100 recites: interpreting a first outcome for the first tracer test based on a difference between the first airflow value and a target airflow value defined for the aerosol zone.

In one implementation, the system can: access a target airflow value defined for the aerosol zone, such as calculated based on a set of environmental characteristics (e.g., size, occupancy, activity type or level) of the aerosol zone; and, in response to the airflow value corresponding to (e.g., matching a value, exceeding a threshold value) the target airflow value, interpret a "pass" outcome for the tracer test. Alternatively, in response to the airflow value differing from the target airflow value, the system can interpret a "fail" outcome for the tracer test.

For example, in response to interpreting a first volumetric airflow rate for the aerosol zone for a first tracer test, the system can: access a target volumetric airflow rate defined for the aerosol zone, such as based on a volume of the aerosol zone, an average or current occupancy level, and/or an activity type (e.g., exercise, eating, sitting, standing, singing, working) associated with the aerosol zone; and, in response to the target volumetric airflow rate exceeding the volumetric airflow rate, interpret a fail outcome for the tracer test. Alternatively, in response to the volumetric airflow rate exceeding and/or matching the target volumetric airflow rate, the system can interpret a pass outcome for the tracer test.

In another implementation, the system can: access a target airflow value defined for the aerosol zone; characterize a difference between the target airflow value and the (observed) airflow value; and, in response to the difference exceeding a threshold difference, interpret a "fail" outcome for the tracer test. Alternatively, in response to the difference falling below the threshold difference, the system can interpret a "pass" outcome for the tracer test. Additionally or alternatively, in another implementation, the system can access a target airflow value defined for the aerosol zone; characterize a difference between the target airflow value and the (observed) airflow value; and calculate an outcome score—such as a quantitative or qualitative score—representative of the difference between the target airflow value and the (observed) airflow value.

7.3.1 Outcome Report

In one variation, the system can generate a report for the tracer test and transmit this report to a user (e.g., a manager, an operator, an administrator) affiliated with the aerosol zone. In particular, in this variation, the system can: generate a first report including the first airflow value and the first outcome; store the first report in a zone profile associated with the aerosol zone; and transmit a copy of the first report to the user (e.g., via the user's mobile device).

Furthermore, in this variation, the system can append the report with a first set of setup data representing a setup configuration defined by the dispenser 110 in the dispenser no location, and a set of sensor units 120—such as including a first sensor unit 120 arranged in a first unit location, a second sensor unit 120 arranged in a second unit location, etc.—installed in a set of unit locations. Later, in preparation for a second tracer test in the aerosol zone, the system can then access the first set of setup data stored in the zone profile; generate a prompt to install the dispenser 110 and the set of sensor units 120—such as including the first sensor unit 120, the second sensor unit 120, etc.—within the aerosol zone according to the setup configuration; and transmit the prompt to the user. The system can therefore promote repeatability of data across tracer tests executed in the aerosol zone, by limiting variations in tracer detection due to modifications in the setup configuration.

7.4 Air Removal Pathways

Generally, the system can leverage airflow values—such as an air change range (e.g., a volumetric airflow rate)—derived for the aerosol zone during execution of the tracer test to derive insights related to various air-removal pathways (or "removal pathways") employed in the aerosol zone.

In particular, the system can implement the methods and techniques described above to derive an airflow value representing air and/or particle removal from the aerosol zone, such as via a set of removal pathways including filtration, ventilation, settling, capture, etc. Therefore, based on the airflow value—and/or the outcome associated with the airflow value (e.g., whether the airflow value corresponds to the target airflow value defined for the aerosol zone)—the system can characterize effectiveness of these removal pathways in the aerosol zone and/or suggest modes of deploying these removal pathways in the aerosol zone.

For example, the system can: execute a first tracer test for the aerosol zone during a first test period, as described above; access a first aerosol removal mode defining a first set of aerosol removal pathways—such as including a first filtration pathway and a first ventilation pathway—employed in the aerosol zone during the first test period; and, in response to interpreting a "fail" outcome for the first tracer test—such as responsive to deriving an airflow value (e.g., an air-change rate or volumetric flowrate) below a target value—withhold verification of the first aerosol removal mode in the aerosol zone. Then, the system can: generate a notification to implement a second aerosol removal mode defining a second set of aerosol removal pathways—such as including a second filtration pathway and a second ventilation pathway—for employing in the aerosol zone during a time period preceding the first test period; and transmit this notification to a user (e.g., an operator, a manager, an administrator) affiliated with the aerosol zone.

Later, the system can: execute a second tracer test for the aerosol zone during a second test period succeeding the first test period—by a target duration—and the time period; interpret a second airflow value based on timeseries aerosol data collected during the second tracer test; and, in response to the second airflow value exceeding the target airflow value, interpret a pass outcome for the second tracer test. The system can then: access the second aerosol removal mode—defining the second set of aerosol removal pathways—employed in the aerosol zone during the second test period; and, in response to interpreting the pass outcome for the second tracer test, verifying the second aerosol removal mode for the aerosol zone. The system can then: generate a second notification to maintain implementation of the second aerosol removal mode in the aerosol zone; and transmit this notification to the user affiliated with the aerosol zone.

In another example, the system can: execute a first tracer test for the aerosol zone during a first test period to derive a first airflow value for an aerosol zone, as described above; and, based on the first outcome—such as in response to the first airflow value falling below a target airflow value—identify a first removal pathway, from a set of removal pathways, configured to drive the first airflow value toward the target airflow value; generate a prompt to implement the first removal pathway in the aerosol zone; and transmit the prompt to a user affiliated with the aerosol zone. Then, during a second test period succeeding the first test period by a target duration, the system can: execute a second tracer test for the aerosol zone during the second test period to derive a second airflow value for the aerosol zone; and characterize effectiveness of the first removal pathway in the aerosol zone based on a first difference between the first airflow value and the second airflow value.

Additionally or alternatively, in one implementation, the system can access a set of environmental controls—such as including HVAC settings, occupancy levels, activity levels or types, etc.—for the aerosol zone, such as before, during, and/or after execution of a tracer test within a test period. In this implementation, the system can leverage results of the tracer test—such as a set of aerosol values derived from timeseries aerosol data collected during execution of the tracer test—to: characterize effectiveness of current environmental controls in the aerosol zone; and/or suggest modifications to current environmental controls, such as to a manager affiliated with the aerosol zone.

For example, during execution of a tracer test within a test period, the system can record a first timeseries of environmental controls, for a first aerosol zone in a facility, such as: a first timeseries of occupancy levels (e.g., number of occupants, occupant density) in the first aerosol zone; a first timeseries of occupancy durations (e.g., duration spent by each occupant in the aerosol zone) in the first aerosol zone; a first timeseries of HVAC data (e.g., temperature, humidity, air filtration rate) in the first aerosol zone; and a first timeseries of intervention data (e.g., windows open or closed, time since last cleaning, type of chemical applied to surfaces). Then, based on timeseries aerosol data collected during execution of the tracer test, the system can interpret a set of airflow values—representing flow and/or movement of aerosols in the aerosol zone during the test period—for the aerosol zone. Based on the set of airflow values, the system can characterize effectiveness (e.g., a percentage, a score out of 100, "highly-effective", "effective", "ineffective", or "detrimental") of the current set of environmental controls—represented in the first timeseries of environmental controls—implemented in the aerosol zone.

Further, in the preceding example, in response to a particular airflow value, in the set of airflow values, falling outside of a threshold deviation of a target metric (e.g., defined for the airflow value), the system can: generate a notification indicating the particular airflow value and including a prompt to modify the HVAC settings—such as according to a particular set of HVAC settings—predicted to drive the particular airflow value toward the target metric.

In one variation, the system can automatically implement modifications to the set of environmental controls in the aerosol zone based on current airflow values and/or risk—associated with a set of pathogens—in the aerosol zone. In particular, in one example, during execution of a tracer test within a test period, the system can access a first set of HVAC settings currently employed by an HVAC system of the aerosol zone. Then, based on timeseries aerosol data collected during execution of the tracer test, the system can interpret a set of airflow values—including a first air-change rate—for the aerosol zone. In response to the first air-change rate falling below a threshold air-change rate defined for the aerosol zone, the system can: select a second set of HVAC settings, in replacement of the first set of HVAC settings, predicted to increase air-change rate in the aerosol zone; and trigger the HVAC system to adjust HVAC settings according to the second set of HVAC settings. Additionally, in this example, the system can execute an additional tracer test—such as after a threshold duration of receiving confirmation of implementation of the second set of HVAC settings by the HVAC system—during a subsequent test period, to verify increase of the air-change rate in the aerosol zone. The system can continue to trigger adjustment of the HVAC settings in the aerosol zone until the air-change rate exceeds the threshold air-change rate defined for the aerosol zone.

8. Tracking Airflow Values Over Time

In one implementation, the system can: track changes in airflow values within the aerosol zone over time; and predict a causal pathway associated with changes in airflow values derived for the aerosol zone.

In particular, in this implementation, the system can: predict a first set of airflow values for the aerosol zone during a first test period based on timeseries aerosol data collected during the first test period, as described above; predict a second set of airflow values for the aerosol zone during a second test period, succeeding the first test period, based on timeseries aerosol data collected during the second test period; characterize a difference between the first set of airflow values and the second set of airflow values; and, based on the difference, predict a causal pathway—such as a change in a particular ventilation technique, in a set of ventilation techniques, employed in the aerosol zone—associated with difference.

For example, during a first test period, the system can: access a first timeseries of aerosol data collected by a first sensor unit 120 arranged in the aerosol zone; access a first set of release parameters corresponding to dispensation of a first test tracer load, during the test period, by a dispenser 110 arranged in the aerosol zone; derive a first tracer signal, representing changes in amounts of tracers of a first type in air detected at the first sensor unit 120 during the first test period, based on the first timeseries of aerosol data and the first set of release parameters; and, based on characteristics of the first tracer signal, predict a first air-change rate for aerosolized particles of the first type in the aerosol zone during the first test period. Then, during a second test period succeeding the first test period, the system can: access a second timeseries of aerosol data collected by the first sensor unit 120; access a second set of release parameters corresponding to dispensation of a second test tracer load, during the second test period, by the dispenser 110; derive a second tracer signal, representing changes in amounts of tracers of the first type in air detected at the first sensor unit 120 during the second test period, based on the second timeseries of aerosol data and the second set of release parameters; and, based on characteristics of the second tracer signal, predict a second air-change rate for aerosolized particles of the first type in the aerosol zone during the second test period. The system can then: characterize a difference between the first and second air-change rates; and, in response to the difference exceeding a threshold difference, predict a first causal pathway—such as a change in HVAC settings within the aerosol zone.

In this implementation, the system can: generate notifications indicating detected changes in airflow values (e.g., an air-change rate) in the aerosol zone; and transmit these notifications to a user or users affiliated with the aerosol zone. For example, in the preceding example, in response to the difference exceeding the threshold difference, the system can: generate a notification—including a prompt to verify or modify the HVAC settings within the aerosol zone—indicating the difference between the first and second air-change rate; and transmit the notification to user affiliated with the aerosol zone.

9. Variation: Tracer Gas+Aerosol Tracers

In one variation, Block S120 of the method S100 recites: releasing a first tracer load into ambient air in an aerosol zone via a dispenser 110 transiently arranged in a target location in the aerosol zone, the first tracer load including a first concentration of aerosol tracer particles and a second concentration of tracer gas. In this variation, Block Silo recites: during execution of the first tracer test within the first test period, recording a first timeseries of aerosol data—representing concentrations of aerosol particles present in air at the first unit location during the first test period—via a first sensor (e.g., an aerosol sensor) integrated in a first sensor unit 120 transiently arranged in a first unit location in the aerosol zone; and recording a second timeseries of gas data via a second sensor (e.g., a gas sensor) transiently arranged in a second location in the aerosol zone, the second timeseries of gas data representing presence of tracer gas in air at the second sensor during the test period.

Generally, in Block Silo, the sensor unit 120 can: access the first sensor (e.g., a particle or aerosol sensor) configured to signal presence of aerosol particles in air; and access the second sensor (e.g., a gas sensor) configured to signal presence of the tracer gas in air. The computer system can: trigger the sensor unit 120 to initiate recording of timeseries aerosol data via the first sensor; and concurrently trigger the sensor unit 120 to initiate recording of timeseries aerosol data via the second sensor. The sensor unit 120 can then implement the methods and techniques described above to: record a timeseries of aerosol data and a timeseries of gas data as described above; write the timeseries of aerosol data and the timeseries of gas data to local storage on the sensor unit 120; and upload the timeseries of aerosol data and the timeseries of gas data to the computer system (e.g., via the sensor communication module 124) at a target logging frequency.

Furthermore, the system can then leverage this data to derive: an aerosol tracer concentration curve representing timeseries concentrations of aerosol tracer particles in the aerosol zone during the test period—based on the timeseries of aerosol data and the first concentration of aerosol particles in the tracer test load—as described above; and implement similar methods and techniques to derive a gas tracer concentration curve—representing timeseries concentrations of tracer gas in the aerosol zone during the test period—based on the timeseries of gas data and the second concentration of tracer gas in the tracer test load.

The system can then leverage these concentration curves to derive: a first airflow value—representative of airborne particle removal from the aerosol zone—based on characteristics (e.g., decay rate, AUC, maximum concentration, minimum concentration, duration of the decay period) of the aerosol concentration curve; and a second airflow value—representative of gas removal from the aerosol zone—based on characteristics (e.g., decay rate, AUC, maximum concentration, minimum concentration, duration of the decay period) of the gas concentration curve.

In particular, the system can: leverage the first airflow value (e.g., a first volumetric airflow)—representative of airborne particle removal from the aerosol zone—to derive insights related to particle removal pathways (e.g., ventilation, settling, capture) associated with particle and/or aerosol removal; and leverage the second airflow value (e.g., a second volumetric airflow)—representative of gas removal from the aerosol zone—to derive insights related to gas removal pathways (e.g., ventilation, settling, capture) associated with gas removal from the aerosol zone. The system can therefore verify gas removal pathways—such as related to ventilation and/or outdoor-air circulation within the indoor environment—independently of particle removal pathways, such as including ventilation and/or outdoor-air circulation, settling, filtering, diluting, etc. Furthermore, based on these airflow value—and/or the outcomes associated with the airflow values (e.g., whether the airflow value corresponds to the target airflow value defined for the aerosol zone)—the system can: characterize effectiveness of various removal pathways corresponding to particles and gases in the aerosol zone; and/or suggest modes of deploying these removal pathways in the aerosol zone.

In one example, the system can implement the methods and techniques described above to: derive an aerosol airflow value representing particle removal from the aerosol zone, such as via a set of removal pathways including filtration, ventilation, settling, capture, etc., based on characteristics of the aerosol concentration curve; derive a gas airflow value representing gas removal from the aerosol zone, such as via a first removal pathway, in the set of removal pathways, corresponding to ventilation (or "outdoor air"), based on characteristics of the gas concentration curve; access a target aerosol flow value defined for aerosol removal in the aerosol zone; access a target airflow value defined for gas removal in the aerosol zone; access a ventilation rate employed by an HVAC system installed in the aerosol zone during the test period; derive a minimum ventilation rate based on the ventilation rate and a difference between the gas airflow value and the target gas airflow value. Then, in response to the aerosol airflow value differing from the target aerosol airflow value, the system can: derive an estimated airflow value representative of particle removal from the aerosol zone during the test period via a first subset of removal pathways, in the set of removal pathways, omitting the first removal pathway; generate a prompt to increase magnitude of the first removal pathway employed in the aerosol zone and predicted to drive the aerosol airflow value toward the target aerosol airflow value; and transmit the prompt to a user affiliated with the aerosol zone.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory 129, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
   during execution of a first tracer test in an aerosol zone within a first test period:
   during a first dispense period, triggering release of a first tracer load into air in the aerosol zone by a dispenser transiently arranged in a dispenser location in the aerosol zone, the first tracer load comprising a test concentration of aerosol tracer particles; and
   recording a first timeseries of aerosol data via a set of sensors integrated in a first sensor unit transiently arranged in a first unit location in the aerosol zone, the first timeseries of aerosol data representing concentrations of aerosol particles present in air at the first unit location during the first test period, recording the first timeseries of aerosol data comprising:
      during a background period preceding the first dispense period, recording a first subset of the first timeseries of aerosol data via the set of sensors; and
      during a decay period succeeding the dispense period, recording a second subset of the first timeseries of aerosol data via the set of sensors;
   based on the first timeseries of aerosol data and the test concentration;
      deriving a baseline concentration of aerosol particles present in the aerosol zone during the first test period based on the first subset of the first timeseries of aerosol data; and
      based on the second subset of the first timeseries of aerosol data and the baseline concentration, deriving a first tracer concentration curve representing change in concentration of aerosol tracer particles at the first unit location during the first test period;
   based on characteristics of the first tracer concentration curve, deriving a first airflow value representing removal of aerosol particles from the aerosol zone during the first test period; and
   interpreting a first outcome for the first tracer test based on a difference between the first airflow value and a target airflow value defined for the aerosol zone.

2. The method of claim 1:
   wherein interpreting the first airflow value based on characteristics of the first tracer concentration curve comprises:
      extracting an area defined by the first tracer concentration curve; and
      deriving the first airflow value comprising a volumetric airflow rate based on the area and a volume of the aerosol zone; and
   wherein interpreting the first outcome for the first tracer test based on the difference between the first airflow value and the target airflow value defined for the aerosol zone comprises:
      accessing the target airflow value comprising a target volumetric airflow rate defined for the aerosol zone; and
      in response to the target volumetric airflow rate exceeding the volumetric airflow rate, interpreting a fail outcome for the first tracer test.

3. The method of claim 1:
   wherein interpreting the first outcome for the first tracer test based on the difference between the first airflow value and the target airflow value comprises, in response to the first airflow value falling below the target airflow value, interpreting a fail outcome for the first tracer test; and
   further comprising:
      accessing a first aerosol removal mode defining a first set of aerosol removal pathways employed in the aerosol zone during the first test period;
      in response to interpreting the fail outcome for the first tracer test, withholding verification of the first aerosol removal mode in the aerosol zone;
      during execution of a second tracer test in the aerosol zone within a second test period succeeding the first test period by a target duration:
         during a second dispense period, triggering release of a second tracer load into air in the aerosol zone by the dispenser transiently arranged in the dispenser location, the second tracer load comprising the test concentration of aerosol tracer particles; and
         recording a second timeseries of aerosol data via the set of sensors integrated in the first sensor unit transiently arranged in the first unit location in the aerosol zone, the second timeseries of aerosol data representing concentrations of aerosol particles present in air at the first unit location during the second test period;
      based on the second timeseries of aerosol data and the test concentration, deriving a second tracer concentration curve representing change in concentration of aerosol tracer particles at the first unit location during the second test period;

based on characteristics of the second tracer concentration curve, deriving a second airflow value representing removal of aerosol particles from the aerosol zone during the second test period;
in response to the second airflow value exceeding the target airflow value, interpreting a pass outcome for the second tracer test;
accessing a second aerosol removal mode defining a second set of aerosol removal pathways employed in the aerosol zone during the second test period; and
in response to interpreting the pass outcome for the second tracer test, verifying the second aerosol removal mode for the aerosol zone.

4. The method of claim 3:
wherein deriving the first airflow value representing removal of aerosol particles from the aerosol zone during the first test period comprises deriving the first air-change rate representing removal of aerosol particles from the aerosol zone during the first test period;
wherein interpreting the fail outcome for the first tracer test in response to the first airflow value falling below the target airflow value comprises interpreting the fail outcome for the first tracer test in response to the first air-change falling below a target air-change rate defined for the aerosol zone;
wherein accessing the first aerosol removal mode defining the first set of aerosol removal pathways comprises accessing the first aerosol removal mode defining the first set of aerosol removal pathways comprising a first filtration pathway and a first ventilation pathway;
wherein deriving the second airflow value representing removal of aerosol particles from the aerosol zone during the second test period comprises deriving the second air-change rate representing removal of aerosol particles from the aerosol zone during the second test period;
wherein interpreting the pass outcome for the second tracer test in response to the second airflow value exceeding the target airflow value comprises interpreting the pass outcome for the second tracer test in response to the second air-change exceeding the target air-change rate; and
wherein accessing the second aerosol removal mode defining the second set of aerosol removal pathways comprises accessing the second aerosol removal mode defining the second set of aerosol removal pathways comprising a second filtration pathway and a second ventilation pathway.

5. The method of claim 1, wherein releasing the first tracer load comprising the test concentration of aerosol tracer particles comprises releasing the first tracer load comprising the test concentration of aerosol tracer particles comprising aerosol salt particles.

6. The method of claim 1, further comprising:
based on the first outcome:
identifying a first removal pathway, from a set of removal pathways, configured to drive the first airflow value toward the target airflow value;
generating a prompt to implement the first removal pathway in the aerosol zone; and
transmitting the prompt to a user affiliated with the aerosol zone;
during a second test period succeeding the first test period by a target duration:
during a second dispense period of the first duration, releasing a second tracer load into air in the aerosol zone via the dispenser, the second tracer load comprising the test concentration of aerosol tracer particles; and
recording a second timeseries of aerosol data via the set of sensors integrated in the first sensor unit, the second timeseries of aerosol data representing concentrations of aerosol particles detected in air at the first unit location during the second test period;
based on the second timeseries of aerosol data and the test concentration, deriving a second tracer concentration curve representing change in concentration of aerosol tracer particles in the aerosol zone during the second test period;
based on characteristics of the second tracer concentration curve, interpreting a second airflow value representative of particle removal from the aerosol zone during the second test period; and
characterizing effectiveness of the first removal pathway in the aerosol zone based on a first difference between the first airflow value and the second airflow value.

7. The method of claim 1:
further comprising:
during the first test period, recording a second timeseries of aerosol data via a second set of sensors integrated in a second sensor unit transiently arranged in a second unit location in the aerosol zone, the second timeseries of aerosol data representing concentrations of aerosol particles present in air at the second unit location during the first test period; and
based on the second timeseries of aerosol data and the test concentration, deriving a second tracer concentration curve representing change in concentration of aerosol tracer particles at the second unit location during the first test period; and
wherein deriving the first airflow value representing removal of aerosol particles from the aerosol zone during the first test period comprises deriving the first airflow value representing removal of aerosol particles from the aerosol zone during the first test period based on characteristics of the first tracer concentration curve and the second tracer concentration curve.

8. The method of claim 7, further comprising:
generating a first report comprising the first airflow value, the first outcome, and a first set of setup data representing a setup configuration defined by the dispenser in the dispenser location, the first sensor unit arranged in the first unit location, and the second sensor unit arranged in the second unit location;
storing the first report in a zone profile associated with the aerosol zone;
at a first time succeeding the first test period by a target duration:
accessing the first set of setup data stored in the zone profile;
generating a prompt to install the dispenser, the first sensor unit, and the second sensor unit within the aerosol zone according to the setup configuration; and
transmitting the prompt to a user affiliated with the aerosol zone;
during execution of a second tracer test within a second test period succeeding the first time:
during a second dispense period of the first duration, releasing a second tracer load into air in the aerosol zone via the dispenser, the second tracer load comprising the test concentration of aerosol tracer particles;
recording a third timeseries of aerosol data via the set of sensors integrated in the first sensor unit, the third timeseries of aerosol data representing concentrations of aerosol particles detected in air at the first unit location during the second test period; and
recording a fourth timeseries of aerosol data via the second set of sensors integrated in the second sensor unit, the fourth timeseries of aerosol data representing concentrations of aerosol particles detected in air at the second unit location during the second test period;
based on the third timeseries of aerosol data and the test concentration, deriving a third tracer concentration curve representing change in concentration of aerosol tracer particles at the first unit location during the second test period;
based on the fourth timeseries of aerosol data and the test concentration, deriving a fourth tracer concentration curve representing change in concentration of aerosol tracer particles at the second unit location during the second test period;
based on characteristics of the third tracer concentration curve and the fourth tracer concentration curve, interpreting a second airflow value representative of particle removal from the aerosol zone during the second test period; and
and characterizing a difference between the first airflow value and the second airflow value.

9. The method of claim 1:
wherein deriving the first airflow value representative of particle removal from the aerosol zone comprises deriving the first airflow value representative of particle removal from the aerosol zone via a set of removal pathways; and
further comprising:
deriving a second airflow value representative of gas removal from the aerosol zone via a first removal pathway, in the set of removal pathways, comprising ventilation;
accessing a target airflow value defined for gas removal in the aerosol zone;
accessing a ventilation rate employed by an HVAC system installed in the aerosol zone during the first test period;
deriving a minimum ventilation rate based on the ventilation rate and a difference between the second airflow value and the target airflow value;
in response to the first airflow value differing from the target airflow value:
based on a difference between the first airflow value and the second airflow value, estimating a third airflow value representative of particle removal from the aerosol zone during the first test period via a first subset of removal pathways, in the set of removal pathways, omitting the first removal pathway;
generating a prompt to increase magnitude of the first removal pathway, in the first subset of removal pathways, employed in the aerosol zone and predicted to drive the first airflow value toward the target airflow value; and
transmitting the prompt to a user affiliated with the aerosol zone.

10. The method of claim 1:
wherein recording the first timeseries of aerosol data representing concentrations of aerosol particles present in air at the first unit location comprises recording the first timeseries of aerosol data representing concentrations of aerosol particles of a first size present in air at the first unit location;
wherein deriving the first tracer concentration curve representing change in concentration of aerosol tracer particles at the first unit location during the first test period comprises deriving the first tracer concentration curve representing change in concentration of aerosol tracer particles of the first size at the first unit location during the first test period;
further comprising:
recording a second timeseries of aerosol data via the set of sensors integrated in the first sensor unit transiently arranged in the first unit location in the aerosol zone, the second timeseries of aerosol data representing concentrations of aerosol particles of a second size, exceeding the first size, present in air at the first unit location during the first test period; and
based on the second timeseries of aerosol data and the test concentration, deriving a second tracer concentration curve representing change in concentration of aerosol tracer particles of the second size at the first unit location during the first test period; and
wherein deriving the first airflow value representing removal of aerosol particles from the aerosol zone during the first test period comprises deriving the first airflow value representing removal of aerosol particles from the aerosol zone during the first test period based on characteristics of the first tracer concentration curve and the second tracer concentration curve.

11. The method of claim 1, wherein characterizing the first airflow score based on the difference between the first airflow value and the target airflow value defined for the aerosol zone comprises:
accessing a set of environment characteristics of the aerosol zone and comprising a first size of the aerosol zone and a target occupancy level defined for the aerosol zone; and
calculating the target airflow value based on the set of environment characteristics.

12. The method of claim 1:
wherein triggering release of the first tracer load by the dispenser transiently arranged in the dispenser location in the aerosol zone comprises triggering release of the first tracer load by the dispenser transiently arranged in the dispenser location in the aerosol zone and comprising:
a reservoir containing salt particles in solution:
an actuator configured to release a tracer test load from the reservoir and into the aerosol zone, the tracer test load comprising a first concentration of aerosol salt particles; and
a first power module configured to supply power to the actuator; and
wherein recording the first timeseries of aerosol data via the set of sensors integrated in the first sensor unit transiently arranged in the first unit location in the aerosol zone comprises recording the first timeseries of aerosol data via the set of sensors integrated in the first sensor unit transiently arranged in the first unit location in the aerosol zone and comprising:
a first set of sensors comprising:
a particle sensor configured to signal presence of aerosol particles in air at the first unit location; and a gas sensor configured to signal presence of the tracer gas in air at the first unit location;
a sensor communication module;
a controller configured to:
read a first timeseries of signals from the particle sensor responsive to a command received by the sensor communication module;
read a second timeseries of signals from the gas sensor responsive to the command;
interpret timeseries amounts of aerosol particles in air flowing through the first unit location based on the first timeseries of signals; and
interpret timeseries amounts of the tracer gas in air flowing through the first unit location based on the second timeseries of signals; and
a second power module configured to supply power to the controller and the first set of sensors.

13. A method comprising:
during execution of a first tracer test in an aerosol zone within a first test period:
during a first dispense period, releasing a first tracer load into ambient air in an aerosol zone via a dispenser transiently arranged in a target location in the aerosol zone, the first tracer load comprising a first concentration of aerosol tracer particles and a second concentration of tracer gas;
recording a first timeseries of aerosol data via a first sensor transiently arranged in a first unit location in the aerosol zone, the first timeseries of aerosol data representing presence of aerosol particles in air at the first sensor during the test period; and
recording a second timeseries of gas data via a second sensor transiently arranged in a second unit location in the aerosol zone, the second timeseries of gas data representing presence of tracer gas in air at the second sensor during the test period;
based on the first timeseries of aerosol data and the first concentration, deriving an aerosol tracer concentration curve representing timeseries concentrations of aerosol tracer particles in the aerosol zone during the test period;
based on characteristics of the aerosol concentration curve, interpreting a first airflow value representative of airborne particle removal from the aerosol zone;
based on the second timeseries of gas data and the second concentration, deriving a gas tracer concentration curve representing timeseries concentrations of tracer gas in the aerosol zone during the test period;
based on characteristics of the gas concentration curve, interpreting a second airflow value representative of gas removal from the aerosol zone;
accessing a first target airflow value representative of airborne particle removal from the aerosol zone;
characterizing a first outcome value for the aerosol zone based on a first difference between the first target airflow value and the first airflow value, the first outcome value indicative of effectiveness of a set of particle removal pathways implemented in the aerosol zone;
accessing a second target airflow value representative of gas removal from the aerosol zone; and
characterizing a second outcome value for the aerosol zone based on a second difference between the second target airflow value and the second airflow value, the second outcome value indicative of effectiveness of a set of gas removal pathways implemented in the aerosol zone.

14. The method of claim 13, further comprising:
in response to the first outcome value corresponding to a target outcome value, verifying effectiveness of the set of particle removal pathways implemented in the aerosol zone; and
in response to the second outcome value differing from the target outcome value:
flagging the set of gas removal pathways for further investigation;
generating a notification indicating the second outcome value and comprising a prompt to modify the set of gas removal pathways implemented in the aerosol zone; and
transmitting the notification to a user affiliated with the aerosol zone.

15. The method of claim 13:
wherein interpreting the first airflow value representative of airborne particle removal from the aerosol zone comprises interpreting the first airflow value representative of airborne particle removal from the aerosol zone via a set of removal pathways;
wherein interpreting the second airflow value representative of gas removal from the aerosol zone comprises interpreting the second airflow value representative of gas removal from the aerosol zone via a first removal pathway, in the set of removal pathways, comprising outdoor-air ventilation; and
further comprising:
characterizing a difference between the first airflow value and the second airflow value;
deriving a third airflow value representative of airborne particle removal from the aerosol zone via a subset of removal pathways, in the set of removal pathways, omitting the first removal pathway; and
calculating a target operating mode for implementation of the subset of removal pathways in the aerosol zone based on the third airflow value.

16. The method of claim 13, wherein releasing the first tracer load comprising the first concentration of aerosol tracer particles and the second concentration of the tracer gas comprises releasing the first tracer load comprising:
the first concentration of aerosol tracer particles comprising aerosolized salt particles; and
the second concentration of the tracer gas comprising isopropyl alcohol.

17. A method comprising:
during execution of a first tracer test in an aerosol zone within a first test period:
during a first dispense period, triggering release of a first tracer load into air in the aerosol zone by a dispenser transiently arranged in a dispenser location in the aerosol zone, the first tracer load comprising a test concentration of aerosol tracer particles; and
recording a first timeseries of aerosol data via a set of sensors integrated in a first sensor unit transiently arranged in a first unit location in the aerosol zone, the first timeseries of aerosol data representing concentrations of aerosol particles present in air at the first unit location during the first test period;
based on the first timeseries of aerosol data and the test concentration, deriving a first tracer concentration curve representing change in concentration of aerosol tracer particles at the first unit location during the first test period;

based on characteristics of the first tracer concentration curve, deriving a first airflow value representing removal of aerosol particles from the aerosol zone during the first test period;

accessing a set of environment characteristics of the aerosol zone and comprising a first size of the aerosol zone and a target occupancy level defined for the aerosol zone;

calculating a target airflow value based on the set of environment characteristics; and interpreting a first outcome for the first tracer test based on a difference between the first airflow value and the target airflow value defined for the aerosol zone.

* * * * *